US008367419B2

(12) United States Patent
Li et al.

(10) Patent No.: US 8,367,419 B2
(45) Date of Patent: Feb. 5, 2013

(54) COMPOSITIONS AND METHODS FOR DETECTION OF EXPLOSIVES

(75) Inventors: Jing Li, Cranbury, NJ (US); Anjian Lan, Fuzhou (CN); Kunhao Li, Princeton, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 221 days.

(21) Appl. No.: 12/824,008

(22) Filed: Jun. 25, 2010

(65) Prior Publication Data
US 2012/0178173 A1 Jul. 12, 2012

Related U.S. Application Data

(60) Provisional application No. 61/220,462, filed on Jun. 25, 2009.

(51) Int. Cl.
G01N 33/00 (2006.01)
C07F 15/00 (2006.01)

(52) U.S. Cl. ........ 436/107; 436/106; 436/110; 436/172; 546/2

(58) Field of Classification Search .......... 436/106–107, 436/110, 172; 546/2
See application file for complete search history.

(56) References Cited

U.S. PATENT DOCUMENTS
2004/0110950 A1* 6/2004 Li et al. ............................. 546/2

OTHER PUBLICATIONS

Fu, Z.-Y. et al, New Journal of Chemistry 2002, 26, 978-980.*
Wang, R. et al, European Journal of Inorganic Chemistry 2004, 37-43.*
Maji, T. K. et al, Angewandte Chemie International Edition 2004, 43, 3269-3272.*
Choi, E.-Y. et al, Chemistry—a European Journal 2004, 10, 5535-5540.*
Wang, R. et al, European Journal of Inorganic Chemistry 2005, 3418-3421.*
Sudik, A. C. et al, Angewandte Chemie International Edition 2006, 45, 2528-2533.*
Chen, B. et al, Inorganic Chemistry 2006, 45, 5718-5720.*
Chen, B. et al, Inorganic Chemistry 2007, 46, 1233-1236.*
Lan, A. et al, Angewandte Chemie International Edition 2009, 48, 2334-2338.*
Davies, et al., "Terahertz spectroscopy of explosives and drugs". Mater. Today 11(3): 18-26. (2008).
Chen, et al., "Luminescent Open Metal Sites within a Metal-Organic Framework for Sensing Small Molecules". Adv. Mater 19: 1693-1696. (2007).
Bauer, et al., "Influence of Connectivity and Porosity on Ligand-Based Luminescence in Zinc Metal-Organic Frameworks". J. Am. Chem. Soc. 129(22): 7136-7144. (2007).
Serre, et al., "Synthesis and Characterization of MIL-79 and MIL-80: Two New Luminescent Open-Framework Rare-Earth Dicarboxylates with Unusual 1D Inorganic Subnetworks". Chem. Mater 16(7): 1177-1182. (2004).
Maspoch, et al., "Old materials with new tricks: multifunctional open-framework materials". Chem. Soc. Rev. 36: 770-818. (2007).

(Continued)

Primary Examiner — Arlen Soderquist
(74) Attorney, Agent, or Firm — Fox Rothschild LLP

(57) ABSTRACT

This invention provides polymeric coordination compounds capable of forming three-dimensional microporous metal organic frameworks (MMOFs) that are useful for detection of explosive compounds. The polymeric coordination compounds comprise a repeating unit comprising a transition metal coordinated to at least one binding member of a bidentate binding site on each of two polyfunctional ligands and one binding site of a bis-pyridine exodentate bridging ligand, for example, the repeating unit comprising formula [$Zn_2$(bpdc)$_2$(bpee)] (bpdc=4,4'-biphenyldicarboxylate; bpee=1,2-bipyridylethene). Methods of preparing such polymeric coordination compounds, methods of using them for detection of explosive compounds, and sensors or sensor arrays comprising such polymeric coordination compounds for detection of explosive compounds, especially those comprising one or more nitro (—$NO_2$) groups, are also disclosed.

25 Claims, 13 Drawing Sheets

OTHER PUBLICATIONS

Tanaka, et al., "Kinetic Gate-Opening Process in a Flexible Porous Coordination Polymer". Angew. Chem. Int. Ed. (47): 3914-3918. (2008).

Thomas, et al., "Chemical Sensors Based on Amplifying Fluorescent Conjugated Polymers". Chem. Rev. 107: 1339-1386. (2007).

Tao, et al., "Metalloporphyrins as sensing elements for the rapid detection of trace TNT vapor". J. Mater. Chem. 16: 4521-4528. (2006).

Maji, et al, "Chemistry of porous coordination polymers". Pure Appl. Chem. 79: 2155-2177. (2007).

Maji, et al., "A flexible interpenetrating coordination framework with a bimodal porous functionality". Nat. Mater. 6: 142-148. (2007).

Andrew, et al, "A Fluorescence Turn-On Mechanism to Detect High Explosives RDX and PETN". J. Am. Chem. Soc. 129: 7254-7255. (2007).

Naddo, et al., "Detection of Explosives with a Fluorescent Nanofibril Film". J. Am. Chem. Soc. 129: 6978-6979. (2007).

Kitagawa, et al., "Functional Porous Coordination Polymers". Angew. Chem. Int. Ed. 43: 2334-2375. (2004).

Thomas, et al., "Amplifying fluorescent polymer sensors for the explosives taggant 2, 3-dimethyl-2,3-dinitrobutane (DMNB)". Chem. Commun. 2005, 4572-4574. (2005).

Naddo, et al., "Highly responsive fluorescent sensing of explosives taggant with an organic nanofibril film". Sensors and Actuators, B: Chemical 134: 287-291. (2008).

Tanaka, et al., "Anthracene array-type porous coordination polymer with host-guest charge transfer interactions in excited states". Chem. Commun. 2007: 3142-3144. (2007).

Ferey, "Hybrid porous solids: past, present, future". Chem. Soc. Rev. 37: 191-214. (2008).

Sohn, et al., "Detection of Nitroaromatic Explosives Based on Photoluminescent Polymers Containing Metalloles". J. Am. Chem. Soc. 125: 3821-3830. (2003).

Steinfeld, et al, "Explosives Detection: A Challenge for Physical Chemistry". Annu. Rev. Phys. Chem. 49 203-232. (1998).

Lee, et al., "Microporous Metal-Organic Frameworks with High Gas Sorption and Separation Capacity". Adv. Funct. Mater. 17: 1255-1262. (2007).

Yang, et al, "Fluorescent Porous Polymer Films as TNT Chemosensors: Electronic and Structural Effects". J. Am. Chem. Soc. 120: 11864-11873. (1998).

Yang, "Porous Shape Persistent Fluorescent Polymer Films: An Approach to TNT Sensory Materials". J. Am. Chem. Soc. 120: 5321-5322. (1998).

Furton, et al., "The scientific foundation and efficacy of the use of canines as chemical detectors for explosives". Talanta 54: 487-500. (2001).

Albert, et al., "Cross-Reactive Chemical Sensor Arrays". Chem. Rev. 100: 2595-2626. (2000).

Wong, et al., "A Highly Porous Luminescent Terbium-Organic Framework for Reversible Anion Sensing". Adv. Mater. 18: 1051-1054. (2006).

Li, et al., "Multifunctional Microporous MOFs Exhibiting Gas/Hydrocarbon Adsorption Selectivity, Separation Capability and Three-Dimensional Magnetic Ordering". Adv. Funct. Mater. 18: 2205-2214. (2008).

L. Pan, et al., "RPM-1: A Recyclable Nanoporous Material Suitable for Ship-In-Bottle Synthesis and Large Hydrocarbon Sorption". Angew. Chem. Int. Ed. 42: 542-546. (2003).

L. Pan, et al., "Separation of Hydrocarbons with a Microporous Metal-Organic Framework". Angew. Chem. Int. Ed. 118: 632-635. (2006).

L. Pan, et al., "RPM-2: A recyclable porous material with unusual adsorption capability: self assembly via structural transformations". Chem Commun 2003: 854-855. (2003).

L. Pan, et al., "Zn(tbip) (H2tbip) 5-tert-Butyl Isophthalic Acid): A Highly Stable Guest-Free Microporous Metal Organic Framework with Unique Gas Separation Capability". J. Am. Chem. Soc. 128: 4180-4181. (2006).

Senesac, et al, "Nanosensors for trace explosive detection". Mater. Today 11: 28-36. (2008).

Germain, et al, "Discrimination of Nitroaromatics and Explosives Mimics by a Fluorescent Zn(salicylaidimine) Sensor Array". J. Am. Chem. Soc. 130: 5422-5423. (2008).

Vallet-Regi, et al., "Mesoporous Materials for Drug Delivery". Angew. Chem. Int. Ed. 46: 7548-7558. (2007).

Yanai, et al., "Reversible Water-Induced Magnetic and Structural Conversion of a Flexible Microporous Ni(II)Fe(III) Ferromagnet". J. Am. Chem. Soc. 129: 3496-3497. (2007).

Yaghi, "Metal-Organic Frameworks: A tale of two entanglements". Nat. Mater. 6: 92-93. (2007).

Ravikovitch, et al, "Density Functional Theory Model of Adsorption on Amorphous and Microporous Silica Materials". Langmuir 22: 11171-11179. (2006).

Tu, et al., "Amine-Capped ZnS-Mn2+ Nanocrystals for Fluorescence Detection of Trace TNT Explosive". Anal. Chem. 80: 3458-3465. (2008).

Toal, et al, "Polymer sensors for nitroaromatic explosives detection". J. Mater. Chem. 16: 2871-2883. (2006).

\* cited by examiner

COMPOSITIONS AND METHODS FOR DETECTION OF EXPLOSIVES

CROSS REFERENCE TO RELATED APPLICATIONS

This application claims the benefit under 35 U.S.C. §119 (e) of U.S. Provisional Application No. 61/220,462, filed on Jun. 25, 2009, which is incorporated herein by reference.

FIELD OF THE INVENTION

The present invention is related to transition metal coordination complexes and three-dimensional microporous metal organic framework made from transition metal coordination compounds for the detection of explosives, as well as methods for the preparation and method of use thereof. In particular, the invention is related to a sensor or sensor array comprising a microporous metal organic framework useful for the detection of explosive compounds.

BACKGROUND OF THE INVENTION

Detection of high explosives is attracting increasing attention due to homeland security, environmental and humanitarian implications. (J. I. Steinfeld and J. Wormhoudt, *Annu. Rev. Phys. Chem.* 1998, 49, 203). 2,4-Dinitrotoluene (DNT), an inevitable by-product in the manufacturing process of 2,4,6-trinitrotoluene (TNT), has a room-temperature vapor pressure about 20 times that of the latter; therefore, the detection of nitroaromatic explosives is often achieved by detection of DNT. On the other hand, plastic explosives often do not contain nitroaromatics, the detection of which is consequently realized by detection of 2,3-dimethyl-2,3-dinitrobutane (DMNB, an taggant required by law to all the commercial plastic explosives). In the search of more convenient and cost-effective alternatives to the well-trained canines (K. G. Furton and L. J. Myers, *Talanta* 2001, 54, 487) or sophisticated analytical instruments (P. Kolla, *Angew. Chem. Int. Ed.* 1997, 36, 801; A. G. Davies, et al., *Mater. Today* 2008, 11, 18), new molecular, oligomeric and polymeric, and nano-scale materials that are capable of fast and reliable sensing of the above chemicals have recently been identified. (See S. W. Thomas, et al., *Chem. Rev.* 2007, 107, 1339; S. J. Toal and W. C. Trogler, *J. Mater. Chem.* 2006, 16, 2871; L. Senesac and T. G. Thundat, *Mater. Today* 2008, 11, 28; R. Y. Tu, et al., *Anal. Chem.* 2008, 80, 3458; T. L. Andrew and T. M. Swager, *J. Am. Chem. Soc.* 2007, 129, 7254; H. Sohn, et al., *J. Am. Chem. Soc.* 2003, 125, 3821; M. E. Germain and M. J. Knapp, *J. Am. Chem. Soc.* 2008, 130, 5422; T. Naddo, et al., *J. Am. Chem. Soc.* 2007, 129, 6978; S. Y. Tao, et al., *J. Mater. Chem.* 2006, 16, 4521.) Fluorescence redox quenching is often the working mechanism within these systems. (S. W. Thomas, et al., *Chem. Rev.* 2007, 107, 1339; S. J. Toal and W. C. Trogler, *J. Mater. Chem.* 2006, 16, 2871). While high to extremely high sensitivity towards nitroaromatic explosives has been demonstrated, detection of DMNB remains a great challenge largely due to its unfavorable reduction potential (−1.7 V vs SCE) and weak binding to the sensory materials because of its three-dimensional molecular structure that lacks of π-π interactions. (S. W. Thomas, J. P. Amara, R. E. Bjork, T. M. Swager, *Chem. Commun.* 2005, 4572).

Microporous metal organic framework (MMOFs) materials are a new class of zeolite-like crystalline materials that have been shown by recent research to have great potential in a wide spectrum of applications, e.g. molecular storage and separation, catalysis, sensing, etc. (G. Ferey, *Chem. Soc. Rev.* 2008, 37, 191; M. Vallet-Regi, et al., *Angew. Chem. Int. Ed.* 2007, 46, 7548; S. Kitagawa, et al., *Angew. Chem. Int. Ed.* 2004, 43, 2334; D. Maspoch, et al., *Chem. Soc. Rev.* 2007, 36, 770; O. M. Yaghi, *Nat. Mater.* 2007, 6, 92; J. Y. Lee, et al., *Adv. Funct. Mater.* 2007, 17, 1255; L. Pan, et al., *J. Am. Chem. Soc.* 2006, 128, 4180; L. Pan, et al., *Angew. Chem. Int. Ed.* 2006, 45, 616; L. Pan, et al., *Angew. Chem. Int. Ed.* 2003, 42, 542; L. Pan, et al., *Chem Commun* (Carob) 2003, 854; K. Li, et al., *Adv. Funct. Mater.* 2008, 18, 2205). A small number of all the MMOFs discovered so far are luminescent in solid state. (C. A. Bauer, et al., *J. Am. Chem. Soc.* 2007, 129, 7136). The combination of luminescence and accessible porosity within such materials imparts them with capability of transducing the host-guest chemistry to observable changes in their luminescence and makes them promising candidates for chemical sensing applications. (B. Chen, et al., *Adv. Mater.* 2007, 19, 1693; K. L. Wong, et al., *Adv. Mater.* 2006, 18, 1051; D. Tanaka, et al., *Chem. Commun.* 2007, 3142; C. Serre, et al., *Chem. Mater.* 2004, 16, 1177). However, to date these MMOF materials have not been reported for detection of explosives.

SUMMARY OF THE INVENTION

This invention demonstrates, for the first time, that a highly luminescent microporous metal organic framework (MMOF) is capable of fast and reversible detection of explosive compounds, such as DNT and DMNB.

In one aspect the present invention provides a polymeric coordination compound capable of forming a microporous metal organic framework (MMOF), characterized by a plurality of layers comprising two-dimensional arrays of repeating structural units, each repeating structural unit comprising at least one transition metal atom or cation (M) coordinated to:

at least one binding member of a bisphenyl-dicarboxylate (bpd) bidentate binding site on each of two polyfunctional ligands of formula (I):

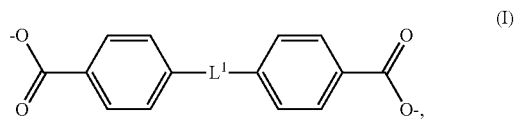

wherein $L^1$ is a bond, —$CH_2$—, —$CHR^1$—$CHR^2$—, or —$CR^1$=$CR^2$—, wherein $R^1$ and $R^2$ are each independently hydrogen (H), methyl, or ethyl group;

one binding site of a bis-pyridine (bp) exodentate bridging ligand of formula (II):

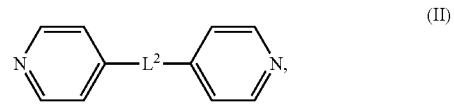

wherein $L^2$ is a —$CH_2$—, —$CHR^1$—$CHR^2$—, or —$CR^1$=$CR^2$—, wherein $R^1$ and $R^2$ are each independently hydrogen (H), methyl, or ethyl group; and said microporous framework has the stoichiometric formula $[M_2(bpd)_2(bp)]$, optionally comprising one or more solvent molecules;

wherein:

(i) at least one binding member of a second bidentate binding site on each polyfunctional ligand is further coordinated to at least one transition metal atom in a different repeating structural unit within the same layer containing a two-dimensional array of repeating structural units;

(ii) the bis-pyridine exodentate bridging ligand extends essentially perpendicularly from a plane defined by said layer containing a two-dimensional array of repeating structural units to further coordinate with a transition metal atom in a repeating structural unit in an adjacent layer; and (iii) the ligands of the three-dimensional MMOF define channels and pores of molecular size throughout the structure of the compound.

In another aspect the present invention provides a method of preparing a polymeric coordination compound as described above, comprising heating a mixture comprising a transition metal salt (M), a ligand of formula (I), and a ligand of formula (II) in a solvent for a period time until a block-like crystal is formed.

In another aspect the present invention provides a method of detecting an explosive compound in a subject, the method comprising:

(a) exposing the subject to a polymeric coordination compound capable of forming a microporous metal organic framework (MMOF) characterized by a plurality of layers comprising two-dimensional arrays of repeating structural units, each repeating structural unit comprising at least one transition metal atom or cation (M) coordinated to:

at least one binding member of a bisphenyl-dicarboxylate (bpd) bidentate binding site on each of two polyfunctional ligands of formula (I):

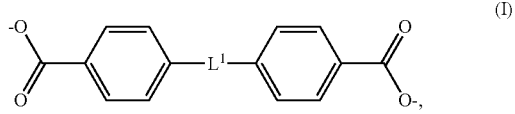

(I)

wherein $L^1$ is a bond, —$CH_2$—, —$CHR^1$—$CHR^2$—, or —$CR^1$=$CR^2$—, wherein $R^1$ and $R^2$ are each independently hydrogen (H), methyl, or ethyl group;

one binding site of a bis-pyridine (bp) exodentate bridging ligand of formula (II):

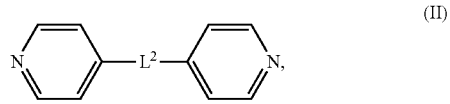

(II)

wherein $L^2$ is a —$CH_2$—, —$CHR^1$—$CHR^2$—, or —$CR^1$=$CR^2$—, wherein $R^1$ and $R^2$ are each independently hydrogen (H), methyl, or ethyl group;

wherein:

(i) at least one binding member of a second bidentate binding site on each polyfunctional ligand is further coordinated to at least one transition metal atom in a different repeating structural unit within the same layer containing a two-dimensional array of repeating structural units;

(ii) the bis-pyridine exodentate bridging ligand extends essentially perpendicularly from a plane defined by said layer containing a two-dimensional array of repeating structural units to further coordinate with a transition metal atom in a repeating structural unit in an adjacent layer; and (iii) the ligands of the three-dimensional MMOF define channels and pores of molecular size throughout the structure of the compound; and (b) observing and/or measuring the change of the luminescence of the polymeric coordination compound, wherein said polymeric coordination compound is luminescent and capable of changing luminescence when in contact with vapors of an explosive compound, and wherein a decreased intensity of the luminescence of the polymeric coordination compound indicates that the subject potentially contains an explosive compound.

In another aspect the present invention provides a sensor or sensor array for detection of explosive compounds comprising a polymeric coordination compound capable forming a microporous metal organic framework (MMOF) as described above.

A preferred embodiment of the MMOF described above comprises an MMOF in which the repeating unit has the structure of formula $[M_2(bpd)_2(bp)]$ (bpd=bisphenyl-dicarboxylate ligand; bp=bispyridine ligand), optionally comprising one or more solvent molecules. An MMOF of this type is capable of fast and highly reversible detection of explosive compounds, such as DNT and DMNB, with unprecedented sensitivity, and the present invention also includes such MMOFs as compositions of matter. In a more preferred embodiment, the bpd has the structure of formula (I) in which $L^1$ is a bond (4,4-biphenyldicarboxylate), bp is 1,2-bipyridylethene (bpee), and M is zinc or cadmium.

Due to the versatility of the porous three-dimensional materials as generally described in US Application Publication No. 2004/0110950, which is incorporated herein by reference, the MMOFs of the present invention may find other broader applications in the host-guest chemistry field than detection of explosive compounds as disclosed herein. For example, they may be used as highly sensitive and selective sensors or sensor arrays.

DETAILED DESCRIPTION OF THE INVENTION

Figure 1:
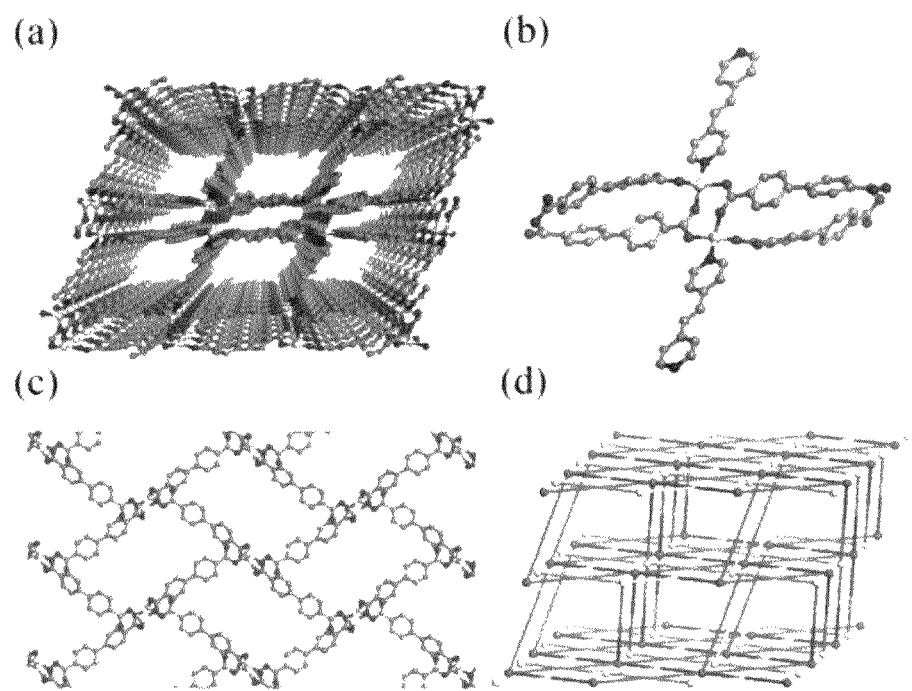
FIG. 1 illustrates (a) perspective view of the 3D structure of 1, showing the channels along b axis (DMF molecules are removed for clarity); (b) the 8-member ring type SBU and the coordination around $Zn^{II}$; (c) a single $4^4$ (brick-like) net; (d) simplified framework connectivity by linking the centroids of SBUs (spheres). The light and dark grey colours highlight the two-fold interpenetration.

The present invention provides polymeric coordination compounds capable of forming microporous metal organic frameworks (MMOFs), which are luminescent and can be used, inter alia, in detection of explosive compounds.

In a first aspect the present invention provides a polymeric coordination compound capable of forming a microporous metal organic framework (MMOF), characterized by a plurality of layers comprising two-dimensional arrays of repeating structural units, each repeating structural unit comprising at least one transition metal atom or cation (M) coordinated to:

at least one binding member of a bisphenyl-dicarboxylate (bpd) bidentate binding site on each of two polyfunctional ligands of formula (I):

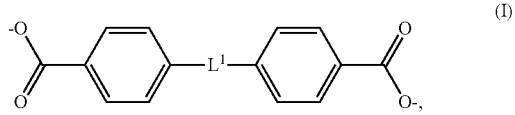

(I)

wherein $L^1$ is a bond, $-CH_2-$, $-CHR^1-CHR^2-$, or $-CR^1=CR^2-$, wherein $R^1$ and $R^2$ are each independently hydrogen (H), methyl, or ethyl group;

one binding site of a bis-pyridine (bp) exodentate bridging ligand of formula (II):

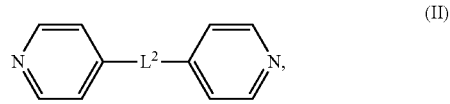

(II)

wherein $L^2$ is a $-CH_2-$, $-CHR^1-CHR^2-$, or $-CR^1=CR^2-$, wherein $R^1$ and $R^2$ are each independently hydrogen (H), methyl, or ethyl group; and said microporous framework has the stoichiometric formula $[M_2(bpd)_2(bp)]$, or a solvate thereof;

wherein:

(i) at least one binding member of a second bidentate binding site on each polyfunctional ligand is further coordinated to at least one transition metal atom in a different repeating structural unit within the same layer containing a two-dimensional array of repeating structural units;

(ii) the bis-pyridine exodentate bridging ligand extends essentially perpendicularly from a plane defined by said layer containing a two-dimensional array of repeating structural units to further coordinate with a transition metal atom in a repeating structural unit in an adjacent layer; and (iii) the ligands of the three-dimensional MMOF define channels and pores of molecular size throughout the structure of the compound.

In one embodiment of this aspect, the present invention provides a polymeric coordination compound as described above, wherein $L^1$ is a bond.

In another embodiment of this aspect, the present invention provides a polymeric coordination compound as described above, wherein $L^2$ is $-CR^1=CR^2-$, wherein $R^1$ and $R^2$ are each independently H, methyl, or ethyl group.

In another embodiment of this aspect, the present invention provides a polymeric coordination compound as described above, wherein the transition metal M is $Zn^{2+}$ or $Cd^{2+}$.

In another embodiment of this aspect, the present invention provides a polymeric coordination compound as described above, wherein:

(a) the ligand of formula (I) is 4,4'-biphenyldicarboxylate (bpdc);

(b) the ligand of formula (II) is 1,2-bipyridylethene (bpee) or 1,2-bipyridylethane (bpe);

(c) the transition metal (M) is $Zn^{2+}$ or $Cd^{2+}$; and (d) said polymeric coordination compound is luminescent and capable of changing luminescence when in contact with vapors of an explosive compound.

In another embodiment of this aspect, the present invention provides a polymeric coordination compound as described above, characterized by formula $[M_2(bpdc)_2(bpee)]$, or a solvate thereof, wherein M is transition metal.

In another embodiment of this aspect, the present invention provides a polymeric coordination compound as described above, characterized by formula $[Zn_2(bpdc)_2(bpee)]$, or a solvate thereof.

In another embodiment of this aspect, the present invention provides a polymeric coordination compound as described above, characterized by formula $[Cd_2(bpdc)_2(bpee)]$, or solvate thereof.

In another embodiment of this aspect, the present invention provides a polymeric coordination compound as described above, characterized by formula $[Zn_2(bpdc)_2(bpee)] \cdot 2DMF$.

In another embodiment of this aspect, the present invention provides a polymeric coordination compound as described above, characterized by formula [Cd$_2$(bpdc)$_2$(bpee)].2DMF.

In another embodiment of this aspect, the present invention provides a polymeric coordination compound as described above, wherein the microporous metal organic framework (MMOF) is luminescent and capable of detecting an explosive compound comprising one or more nitro (—NO$_2$) groups.

In another embodiment of this aspect, the present invention provides a polymeric coordination compound as described above, wherein the microporous metal organic framework (MMOF) is luminescent and capable of detecting an explosive compound selected from 2,4-dinitrotoluene (DNT), 2,4,6-trinitrotoluene (TNT), 2,3-dimethyl-2,3-dinitrobutane (DMNB), and cyclotrimethylene-trinitramine (RDX).

In a second aspect the present invention provides a method of preparing a polymeric coordination compound capable of forming a microporous metal organic framework (MMOF), characterized by a plurality of layers comprising two-dimensional arrays of repeating structural units, each repeating structural unit comprising at least one transition metal atom or cation (M) coordinated to:

at least one binding member of a bisphenyl-dicarboxylate (bpd) bidentate binding site on each of two polyfunctional ligands of formula (I):

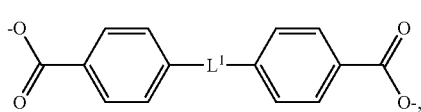
(I)

wherein L$^1$ is a bond, —CH$_2$—, —CHR$^1$—CHR$^2$—, or —CR$^1$=CR$^2$—, wherein R$^1$ and R$^2$ are each independently hydrogen (H), methyl, or ethyl group;

one binding site of a bis-pyridine (bp) exodentate bridging ligand of formula (II):

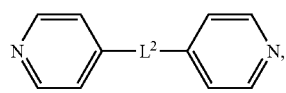
(II)

wherein L$^2$ is a —CH$_2$—, —CHR$^1$—CHR$^2$—, or —CR$^1$=CR$^2$—, wherein R$^1$ and R$^2$ are each independently hydrogen (H), methyl, or ethyl group; and said microporous framework has the stoichiometric formula [M$_2$(bpd)$_2$(bp)], or a solvate thereof;
wherein:

(i) at least one binding member of a second bidentate binding site on each polyfunctional ligand is further coordinated to at least one transition metal atom in a different repeating structural unit within the same layer containing a two-dimensional array of repeating structural units;

(ii) the bis-pyridine exodentate bridging ligand extends essentially perpendicularly from a plane defined by said layer containing a two-dimensional array of repeating structural units to further coordinate with a transition metal atom in a repeating structural unit in an adjacent layer; and (iii) the ligands of the three-dimensional MMOF define channels and pores of molecular size throughout the structure of the compound.

In one embodiment of this aspect, the present invention provides a method for preparation of a polymeric coordination compound as described above, wherein said polymeric coordination compound comprises a structure of formula [M$_2$(bpdc)$_2$(bpee)], which optionally comprises one or more solvent molecules, wherein bpdc is 1,4-biphenyldicarboxylic acid, and bpee is 1,2-bipyridylethene.

In another embodiment of this aspect, the present invention provides a method for preparation of a polymeric coordination compound as described above, wherein the transition metal salt is zinc nitrate (Zn(NO$_3$)$_2$) or a solvate thereof, the ligand of formula (I) is H$_2$bpdc, and the ligand of formula (II) is bpee.

In another embodiment of this aspect, the present invention provides a method for preparation of a polymeric coordination compound as described above, wherein the block-like crystal comprises a repeating unit having a structure of formula [Zn$_2$(bpdc)$_2$(bpee)] or a solvate thereof.

In another embodiment of this aspect, the present invention provides a method for preparation of a polymeric coordination compound as described above, wherein the transition metal salt is zinc nitrate (Zn(NO$_3$)$_2$) or a solvate thereof, the ligand of formula (I) is H$_2$bpdc, and the ligand of formula (II) is bpee.

In another embodiment of this aspect, the present invention provides a method for preparation of a polymeric coordination compound as described above, wherein said block-like crystal comprises a three-dimensional (3-D) framework structure in monoclinic space group C2/c.

In another embodiment of this aspect, the present invention provides a method for preparation of a polymeric coordination compound as described above, wherein said block-like crystal comprises a 3-D structure characterized by FIG. 1a.

In a third aspect the present invention provides a method of detecting an explosive compound in a subject, the method comprising:

(a) exposing the subject to a polymeric coordination compound capable of forming a microporous metal organic framework (MMOF) characterized by a plurality of layers comprising two-dimensional arrays of repeating structural units, each repeating structural unit comprising at least one transition metal atom or cation (M) coordinated to:

at least one binding member of a bisphenyl-dicarboxylate (bpd) bidentate binding site on each of two polyfunctional ligands of formula (I):

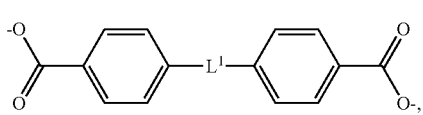
(I)

wherein L$^1$ is a bond, —CH$_2$—, —CHR$^1$—CHR$^2$—, or —CR$^1$=CR$^2$—, wherein R$^1$ and R$^2$ are each independently hydrogen (H), methyl, or ethyl group;

one binding site of a bis-pyridine (bp) exodentate bridging ligand of formula (II):

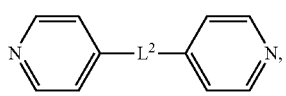
(II)

wherein L² is a —CH₂—, —CHR¹—CHR²—, or —CR¹=CR²—, wherein R¹ and R² are each independently hydrogen (H), methyl, or ethyl group;

wherein:

(i) at least one binding member of a second bidentate binding site on each polyfunctional ligand is further coordinated to at least one transition metal atom in a different repeating structural unit within the same layer containing a two-dimensional array of repeating structural units;

(ii) the bis-pyridine exodentate bridging ligand extends essentially perpendicularly from a plane defined by said layer containing a two-dimensional array of repeating structural units to further coordinate with a transition metal atom in a repeating structural unit in an adjacent layer; and (iii) the ligands of the three-dimensional MMOF define channels and pores of molecular size throughout the structure of the compound; and (b) observing and/or measuring the change of the luminescence of the polymeric coordination compound, wherein said polymeric coordination compound is luminescent and capable of changing luminescence when in contact with vapors of an explosive compound, and wherein a decreased intensity of the luminescence of the polymeric coordination compound indicates that the subject potentially contains an explosive compound.

In one embodiment of this aspect, the present invention provides a method detecting an explosive compound, wherein:

L¹ is a bond, —CH₂—, —CH=CH— or —CH₂CH₂—; and

L² is —CR¹=CR²—, wherein R¹ and R² are each independently hydrogen (H), methyl, or ethyl group.

In one embodiment of this aspect, the present invention provides a method detecting an explosive compound, wherein said MMOF comprises a repeating unit comprising a structure of formula [M₂(bpdc)₂(bpee)] (bpdc=4,4'-biphenyldicarboxylate; bpee=1,2-bipyridylethene), optionally comprising one or more solvent molecules, wherein M is a transition metal cation.

In another embodiment of this aspect, the present invention provides a method detecting an explosive compound, wherein the transition metal M is Zn²⁺ or Cd²⁺.

In another embodiment of this aspect, the present invention provides a method detecting an explosive compound, wherein the transition metal M is Zn²⁺, and wherein said MMOF comprises a three-dimensional structure characterized by FIG. 1a.

In another embodiment of this aspect, the present invention provides a method detecting an explosive compound, wherein said explosive compound comprises one or more nitro (—NO₂) groups.

In another embodiment of this aspect, the present invention provides a method detecting an explosive compound, wherein said explosive compound is selected from the group consisting of 2,4-dinitrotoluene (DNT), 2,4,6-trinitrotoluene (TNT), 2,3-dimethyl-2,3-dinitrobutane (DMNB), and cyclotrimethylene-trinitramine (RDX).

In a fourth aspect the present invention provides a sensor or sensor array for detection of explosive compounds comprising a polymeric coordination compound capable forming a microporous metal organic framework (MMOF), characterized by a plurality of layers comprising two-dimensional arrays of repeating structural units, each repeating structural unit comprising at least one transition metal atom or cation (M) coordinated to:

at least one binding member of a bisphenyl-dicarboxylate (bpd) bidentate binding site on each of two polyfunctional ligands of formula (I):

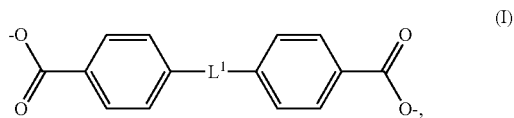

wherein L¹ is a bond, —CH₂—, —CHR¹—CHR²—, or —CR¹=CR²—, wherein R¹ and R² are each independently hydrogen (H), methyl, or ethyl group;

one binding site of a bis-pyridine (bp) exodentate bridging ligand of formula (II):

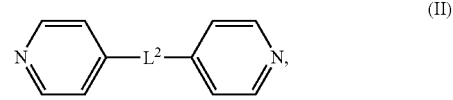

wherein L² is a —CH₂—, —CHR¹—CHR²—, or —CR¹=CR²—, wherein R¹ and R² are each independently hydrogen (H), methyl, or ethyl group; and said microporous framework has the stoichiometric formula [M₂(bpd)₂(bp)], or a solvate thereof;

wherein:

(i) at least one binding member of a second bidentate binding site on each polyfunctional ligand is further coordinated to at least one transition metal atom in a different repeating structural unit within the same layer containing a two-dimensional array of repeating structural units;

(ii) the bis-pyridine exodentate bridging ligand extends essentially perpendicularly from a plane defined by said layer containing a two-dimensional array of repeating structural units to further coordinate with a transition metal atom in a repeating structural unit in an adjacent layer; and (iii) the ligands of the three-dimensional MMOF define channels and pores of molecular size throughout the structure of the compound.

In one embodiment of this aspect, the present invention provides a sensor or sensor array for detection of explosive compounds, wherein said polymeric coordination compound comprises a repeating unit characterized by formula [M₂(bpdc)₂(bpee)] (bpdc=4,4'-biphenyldicarboxylate; bpee=1,2-bipyridylethene), wherein M is a transition metal cation, and wherein said polymeric coordination compound is luminescent and capable of changing luminescence when in contact with vapors of an explosive compound.

In another embodiment of this aspect, the present invention provides a sensor or sensor array for detection of explosive compounds, wherein the transition metal is Zn²⁺ or Cd²⁺.

In another embodiment of this aspect, the present invention provides a sensor or sensor array for detection of explosive compounds, wherein said polymeric coordination compound comprises a repeating unit comprising a structure of formula [M₂(bpdc)₂(bpee)] (bpdc=4,4'-biphenyldicarboxylate; bpee=1,2-bipyridylethene), wherein M is Zn²⁺ or Cd²⁺, and wherein said polymeric coordination compound is luminescent and capable of changing luminescence when in contact with vapors of an explosive compound.

In another embodiment of this aspect, the present invention provides a sensor or sensor array for detection of explosive compounds, wherein said polymeric coordination compound comprises a repeating unit comprising a structure of formula [$Zn_2(bpdc)_2(bpee)$] (bpdc=4,4'-biphenyldicarboxylate; bpee=1,2-bipyridylethene), and said polymeric coordination compound comprises a three-dimensional structure characterized by FIG. 1a.

In another embodiment of this aspect, the present invention provides a sensor or sensor array for detection of explosive compounds, wherein said explosive compound comprises one or more nitro ($-NO_2$) groups.

In another embodiment of this aspect, the present invention provides a sensor or sensor array for detection of explosive compounds, wherein said explosive compound is selected from the group consisting of 2,4-dinitrotoluene (DNT), 2,4,6-trinitrotoluene (TNT), 2,3-dimethyl-2,3-dinitrobutane (DMNB), and cyclotrimethylene-trinitramine (RDX).

The microporous metal organic framework (MMOF) materials according to the present invention are three-dimensional polymeric coordination compounds characterized by a plurality of layers of essentially two-dimensional arrays of repeating structural units, each repeating structural unit having at least one transition metal atom coordination bonded to one binding site of an exodentate bridging ligand and at least one binding member of a bidentate binding site on each of two polyfunctional ligands.

In the repeating structural units the transition metal atom has coordination sites arranged geometrically about it. For example, an octahedral arrangement of coordination sites has four coordination sites located in a plane, equidistant from the metal center (occupying the corners of a square, the metal centered in the square), and two additional coordination sites, one located above and one below the plane, centered over the metal center. A second example is a trigonal bipyramidal arrangement of coordination sites, which involves three coordination sites in a plane equidistant from a metal center (occupying the corners of an equilateral triangle, metal centered in the triangle) with two additional coordination sites, one located above and one below the plane and centered over the metal.

In coordination compounds, the coordination sites about the metal center are occupied by ligands. Ligands can be atoms, molecular fragments, or molecules, with or without an electron charge. Ligands have binding sites. A ligand binding site is an atom or group of atoms in close proximity on the ligand that interacts with one or more coordination sites of the metal center.

The number of coordination sites on a metal center which can be occupied by a given binding site of a ligand is the ligand's dentate number. Thus, a ligand having a binding site which can only occupy one coordination site on a metal center is monodentate, a ligand having a binding site which can occupy two coordination sites on a metal center is bidentate, and so forth.

Polydentate binding sites, for example a bidentate binding site, are essentially a group of monodentate binding sites arranged in a ligand such that they can interact simultaneously with multiple coordination sites on one metal center. This is to say that a bidentate binding site has two atoms which can interact with a metal center to form a coordinate bond and are in sufficiently close proximity and geometrically disposed such that both atoms of the bidentate ligand binding site can participate in the occupation of two coordination sites (one atom in each site) of a single metal atom. Alternately the binding members can occupy one coordination site on each of two metal atoms in close proximity.

Examples of such ligands are those containing a carboxylate, phosphate, sulfate, nitrate, diamino, or amide functional groups. It will be appreciated that other types of binding sites comprising oxygen and/or nitrogen atoms arranged such that two of either atoms are proximate and properly geometrically disposed to each other will also constitute bidentate binding sites.

As used herein, each atom of a polydentate binding site on a ligand is referred to as a coordinating member of that binding site. Further, as used herein, a polydentate binding site on a ligand is distinct from a ligand which has multiple monodentate binding sites, for example, an exodentate ligand, further described below.

A ligand with multiple monodentate binding sites can interact with a single coordination site on several different transition metal centers at the same time, but it can not interact with more than one coordination site on a single metal center at one time. For example, the oxygen atoms of a dicarboxylate group constitute a bidentate binding site with each oxygen atom constituting a coordinating member of that binding site, and the nitrogen atoms of a bispyridine (bp) ligand such as 4,4'-bipyridine (bpy), or a bispyridine ligand comprising a short linker between the two pyridine groups connecting the carbon atoms at the respective 4-position of the pyridine rings, constitute two monodentate binding sites in the bispyridine ligand. The oxygen atoms of the dicarboxylate binding site are geometrically disposed so that both can simultaneously interact with a different coordination site on a single transition metal center but 4,4'-bipyridine cannot be distorted to bring both nitrogen atoms into the geometrical alignment necessary for both nitrogen atoms to simultaneously interact with two coordination sites on one transition metal.

As mentioned above, the porous, three-dimensional compounds of the present invention are formed of layers, each characterized by a two-dimensional array of repeating structural units that are interbonded by exodentate ligands coordinated between two transition metal atoms, each located in a repeating structural unit in an adjacent layer. Each two-dimensional array layer of repeating structural units has transition metal centers bonded together by polyfunctional ligands. The polyfunctional ligands extend in two directions, e.g., the x and y axis of a plane defining the two dimensional array layer, and form coordination bonds between transition metal centers in two different repeating structural units using coordinating members of two different polydentate sites on the ligand (thus, an essentially two-dimensional array of repeating structural units).

The planarity of the layer itself can vary with respect to the alignment and bond angles of the constituents of the repeating structural units. It will be appreciated that the term layer includes a range of structural configurations ranging between a strictly planar arrangement of the constituents of the layer to an arrangement in which the constituents can be above and below a plane defined by the layer by a distance on the order of a dimension of a repeating structural unit.

The structure of the polymeric coordination compounds of the present invention extends in a third direction, e.g., along a z axis perpendicular to the x, y plane described above, by co-ordination bonding of exodentate ligands. The exodentate ligands extend essentially perpendicularly from the plane defined by the two-dimensional array of repeating structural units along the z axis to form bonds between the transition metal atoms of two adjacent layers of two-dimensional arrays of repeating structural units using two different monodentate binding sites on the ligand, thus forming a bridge bonding together adjacent two-dimensional array layers of repeating structural units.

The properties of transition metal compounds and of the metal atom(s) and coordinated ligands comprising such compounds are often described in terms of the hard, soft, or borderline acid or base character of the transition metal and its ligands. This concept is described, for example, by Pearson in *Mechanisms of Inorganic Reactions, a Study of Metal Complexes in Solution*, (Wiley & Sons, New York, 1967), and in *Inorganic Chemistry, Principles of Structure and Reactivity*, (3rd Ed., James E. Huheey). Not being bound by theory, transition metal atoms suitable for use in compounds of the present development are selected from transition metals having at least one stable oxidation state classified under the Pearson categories as a soft or borderline acid, for example, iron, cobalt, nickel, zinc, cadmium, palladium, and platinum in the +2 oxidation state, and which are capable of forming (in any oxidation state) stable complexes with ligands classified under the Pearson categories as hard or borderline bases, for example, those which include in their structure one or more nitrogen or oxygen atoms that are available for coordination to a metal center.

The polyfunctional ligand compounds suitable for use in the compounds of the present invention have at least one ligand containing at least two bidentate binding sites disposed in the ligand structure. The bidentate sites of suitable polyfunctional ligand compounds are positioned so that if each of two different transition metal centers are bonded to one bidentate binding site, the resulting structure has an essentially co-linear arrangement of the ligand and metal atoms with the metal atoms located between about 4 angstroms and about 20 angstroms apart.

Further, suitable polyfunctional ligand compounds are characterized as being "rigid," and therefore not capable of having a conformation that provides for close proximity of these two bi-dentate binding sites. Ligands having in their structure more than two binding sites are also con-templated, provided that at least two binding sites are bidentate and arranged to give an essentially co-linear disposition of the ligand and two metal atoms bound to the bidentate binding sites.

Preferably, the polyfunctional ligand compound used in the pillared, porous, three-dimensional polymeric coordination compounds of the present development have only two bidentate binding sites, but ligands having more than two bidentate binding sites are contemplated, as well as those which have polydentate binding sites and additionally, one or more monodentate binding sites. An example of a polyfunctional ligand compound suitable for use in compounds of the present development is biphenyl-4,4'-dicarboxylate (bpdc).

The porous three-dimensional polymeric compounds of the present invention can be described as pillared compounds, with exodentate ligand pillars bonding layers of two-dimensional arrays of repeating structural units together. Exodentate ligands are compounds having at least two mono-dentate binding sites, which are disposed in the ligand compound structure such that two different metal atoms, one bonded to each binding site, and the remaining ligand compound structure are essentially co-linear. Suitable exodentate ligand compounds are also characterized as having a rigid structure, which means that they cannot assume a conformation that places the two binding sites proximal to each other.

The binding sites of exodentate ligand compounds suitable for use in compounds of the present invention are characterized in terms of the Pearson categories described above as hard or borderline bases and are further characterized as "good pi-backbonding ligands," as that term is defined in *Principles and Applications of Organotransition Metal Chemistry*, (Coleman and Hegedus, University Science Books, Mill Valley, Calif., 1980). An example of a suitable exodentate bridging ligand compound is 4,4'-bipyridine, wherein the pyridine moieties are connected by a spacer or a linker. The linker is preferably a divalent, unsaturated moiety, such as vinylene, which can form conjugation with the two pyridine rings.

Thus, the porous three-dimensional compound of the instant invention contains layers of a poly-functional ligand such as, for example, biphenyl-4,4'-dicarboxylate forming coordination bonds with a transitional metal, with cobalt and zinc being the most preferred transition metals for use in polymeric compounds of the present invention. The layers of the polyfunctional ligand are connected through exodentate ligand pillars, which also form coordination bonds with the transitional metal, thereby forming a porous three-dimensional layered structure containing channels or pores of molecular size.

Figure 5:
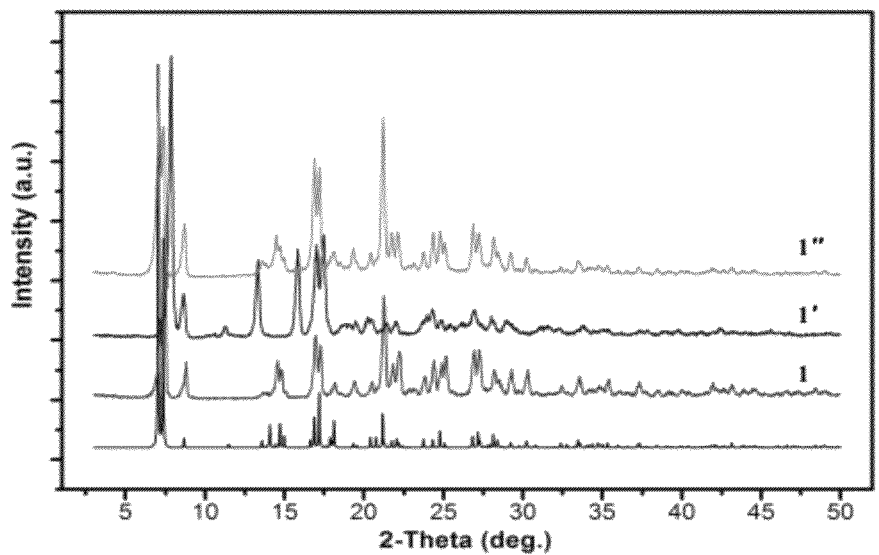
FIG. 5 depicts powder X-ray diffraction patterns of an as-made sample of 1, 1' and a sample of 1' after being heated in DMF at 80° C. for 6 hours (1"). The pattern in black (bottom) is the calculated pattern from the single crystal structure of 1.
Figure 6:
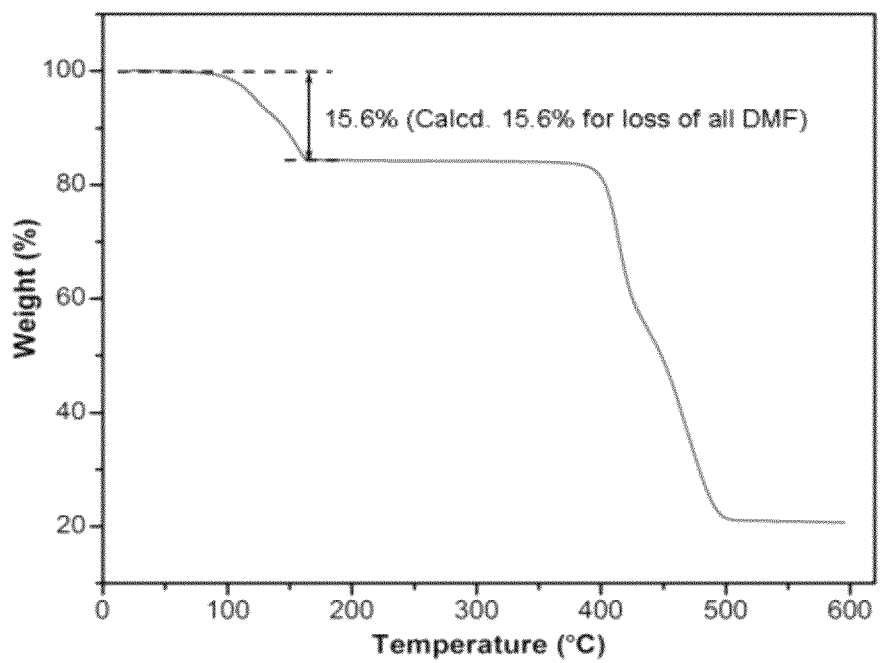
FIG. 6 depicts thermogravimetric analysis of a freshly prepared sample of 1 showing a good match of the observed weight loss due to DMF removal with the calculated weight of DMF.

One particular compound forming the microporous metal organic framework (MMOF) is $Zn_2(bpdc)_2(bpee)\cdot2DMF$ (1) or its guest-free form $Zn_2(bpdc)_2(bpee)$ (1'), in which the bpdc has the structure of Formula (I) wherein $L^1$ is a bond. The structure of $Zn_2(bpdc)_2(bpee)\cdot2DMF$ (1) is a flexible, porous three-dimensional (3D) network composed of one-dimensional (1D) open channels running along the crystallographic b-axis. The size of the parallelogram shaped pore window is ~5×7 Å (excluding van der Waals radius of carbon, 1.7 Å). The solvent accessible volume was calculated to be 1171.9 Å$^3$ (27.6% of the unit cell volume) and the micropore volume, 0.171 cc/g based on the 77K $N_2$ adsorption isotherm data (See FIGS. 4A and 4B). The structure is highly flexible and undergoes a fully reversible change after removal and refill of DMF guest molecules (See FIGS. 5 and 6). This high structural flexibility leads to a well documented gate opening-closing phenomenon, as evident in both Ar and $N_2$ isotherms at 87 and 77K, respectively.

Colorless block-like crystals of $[Zn_2(bpdc)_2(bpee)]\cdot2DMF$ (1) were grown solvothermally. Single crystal X-ray diffraction study disclosed a three-dimensional (3D) framework structure in monoclinic space group C2/c. The overall structure can be viewed as bpee ligands pillaring the undulating charge-neutral $[Zn_2(bpdc)_2]$ layers (FIG. 1a). Two $\mu_2$ bidentate carboxylate groups from two centro-symmetrically related bpdc ligands coordinate to two $Zn^{II}$ to form $Zn_2(COO)_2^{2+}$ corrugated 8-member ring type secondary building unit or SBU (FIG. 1b). Two monodentate carboxylates from another pair of centro-symmetrically related bpdc coordinate to the two $Zn^{II}$ centers respectively, balancing the charges on the bi-zinc SBU. Thus each SBU becomes a 4-connecting node, which is linked by bpdc ligands to four other SBUs to form the two-dimensional $4^4$ (brick-like) net as shown in FIG. 1c. (A. F. Wells, *Three-dimensional Nets and Polyhedra*, John Wiley & Sons, New York, London, Sydney, Toronto, 1977). Interpenetration of two such $4^4$ nets leads to a $[Zn_2(bpdc)_2]$ layer. Bpee ligands coordinate to $Zn^{II}$ centers in two neighboring layers, completing the tetrahedral coordination sphere for each $Zn^{II}$ and connecting the layers into the overall 3D structure. It should be noted that all bpdc ligands within the layers, as well as the bpee ligands connecting the layers, are well separated. No significant π-π interactions are observed within the framework (the closest carbon atoms within the π systems of bpdc and bpee are ~3.8 Å and ~4.6 Å apart, respectively). While the bpdc ligands are bent and twisted to accommodate the interpenetration, bpee ligands remain essentially co-planar.

The present invention is described more fully by way of the following illustrative, non-limiting examples.

EXAMPLES

Example 1

Materials and Methods

A mixture of $Zn(NO_3)_2 \cdot 6H_2O$ (0.0892 g, 0.30 mmol), $H_2$bpdc (0.0727 g, 0.30 mmol) and bpee (0.0547 g, 0.30 mmol) in DMF (15 mL) was heated at 165° C. for 3 days to afford colorless block-like crystals (1, 58% yield). A freshly made sample of 1 was immersed into methanol (3 days) and dichloromethane (4 days) consecutively for solvent exchange, followed by pumping at room temperature to afford 1'.

2,4-dinitrotoluene (99%) and 2,3-dimethyl-2,3-dinitrobutane (98%) were purchased from TCI America and used as received. About 1 g of each were placed into two small open vials and the vials were placed into two capped bottles four days before the fluorescence quenching experiments to ensure equilibrated vapor pressures were reached. The original fluorescence spectra of the layers (see Example 5 for the preparation of the layers) were collected (the peak intensities of which were used to correct the effects of variations in layer thickness and morphology) before placing the layers into the bottles containing the analytes. At the specified exposure time, one layer was taken out and quickly mounted to the sample holder of a Varian Cary Eclipse fluorescence spectrophotometer and the fluorescence spectrum was collected without delay.

SEM images were taken on an Amray 1830 I scanning electron microscope (the samples were coated with a thin layer of gold-palladium before-hand for better contrast). Single crystal X-ray diffraction data of 1 were collected at 293(2) K on a Bruker-AXS smart APEX I CCD diffractometer with graphite-monochromated Mo Kα radiation ($\lambda$=0.71073 Å). A total of 18781 reflections were collected (4349 unique, R(int)=0.0474) between a θ of 2° to 26.37°. The structure was solved by direct methods and refined by full-matrix least-squares on $F^2$ using the Bruker SHELXTL package. R1=0.0447 (I>2σ(I)), wR2=0.1047 (all data), GoF=1.007 (all data). Crystal data for 1: $C_{46}H_{40}N_4O_{10}Zn_2$, f.w.=939.56 g mol$^{-1}$, monoclinic, C2/c, a=26.138(2) Å, b=6.7464(4) Å, c=25.024(2) Å, β=105.916(1)°, V=4243.4(4) Å$^3$, Z=4, $\rho_{calcd.}$=1.471 g·cm$^{-3}$. CCDC-704475. Other selected crystallographic data are listed in Table 1.

TABLE 1

| Selected Crystallographic Data for 1. | |
|---|---|
| Identification code | aj12f |
| Empirical formula | C46H40N4O10Zn2 |
| Formula weight | 939.56 |
| Temperature | 293(2) K |
| Wavelength | 0.71073 Å |
| Crystal system | Monoclinic |
| Space group | C2/c |
| Unit cell dimensions | a = 26.1377(16) Å   α = 90°. |
| | b = 6.7464(4) Å   β = 105.916(1)°. |
| | c = 25.0235(15) Å   γ = 90°. |
| Volume | 4243.4(4) Å$^3$ |
| Z | 4 |
| Density (calculated) | 1.471 Mg/m$^3$ |
| Absorption coefficient | 1.195 mm$^{-1}$ |
| F(000) | 1936 |
| Crystal size | 0.21 × 0.05 × 0.01 mm$^3$ |
| Theta range for data collection | 2.00 to 26.37°. |
| Index ranges | −32 <= h <= 32, −8 <= k <= 8, −31 <= l <= 31 |
| Reflections collected | 18781 |
| Independent reflections | 4349 [R(int) = 0.0474] |
| Completeness to theta = 26.37° | 100.0% |
| Absorption correction | Semi-empirical from equivalents |
| Max. and min. transmission | 0.9999 and 0.8804 |
| Refinement method | Full-matrix least-squares on $F^2$ |
| Data/restraints/parameters | 4349/0/282 |
| Goodness-of-fit on $F^2$ | 1.007 |
| Final R indices [I > 2sigma(I)] | R1 = 0.0447, wR2 = 0.0969 |
| R indices (all data) | R1 = 0.0616, wR2 = 0.1047 |
| Largest diff. peak and hole | 0.427 and −0.272 e · Å$^{-3}$ |

Example 2

PXRD and TGA

Powder X-ray diffraction patterns of all samples were recorded on a Rigaku D/M-2200T automated diffractometer (Ultima+) using Cu Kα radiation ($\lambda$=1.5406 Å). The patterns were collected between a 2θ of 3° to 50° at a scan speed of 4 deg/min. Graphite monochromator was used and the generator power settings are at 40 kV and 40 mA. Thermogravimetric analysis was carried out on the TA Q50 thermal gravimetric analyzer with nitrogen flow rate and sample purge rate set at 40 mL/min and 60 mL/min, respectively. The temperature was ramped from room temperature to 600° C. at 20° C./min.

As indicated by the intense and sharp PXRD peaks, 1' remains highly crystalline although there are obvious shift of the peaks and emergence of new peaks. It is believed that this is caused by the distortion of the unit cell, resulting in a structure of lower symmetry, instead of collapse of the original structure, which usually leads to disappearance (or at least severe broadening) of the PXRD peaks.

The structure of 1' can be easily reversed to that of 1 by simply heating a sample of 1' in DMF at 80° C. for 6 hours. This condition is much milder compared to the synthetic (crystal growth) conditions for 1 (165° C. for 3 days). This is further evidence that the structure of 1' represents distortion instead of collapse of the structure of 1. It also shows that the transition between the two structures is facile (as also evidenced by the benzene adsorption measurement and simulation results below).

Example 3

Gas (Argon) Sorption and Pore Characterization

Figure 7:
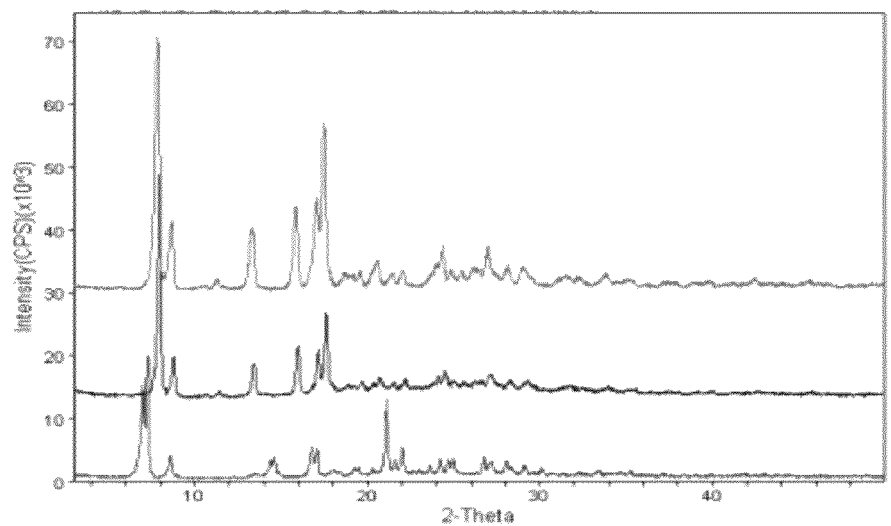
FIG. 7 depicts PXRD patterns for the as-made (bottom), activated sample before isotherms (middle) and after isotherms (top).
Figure 8:
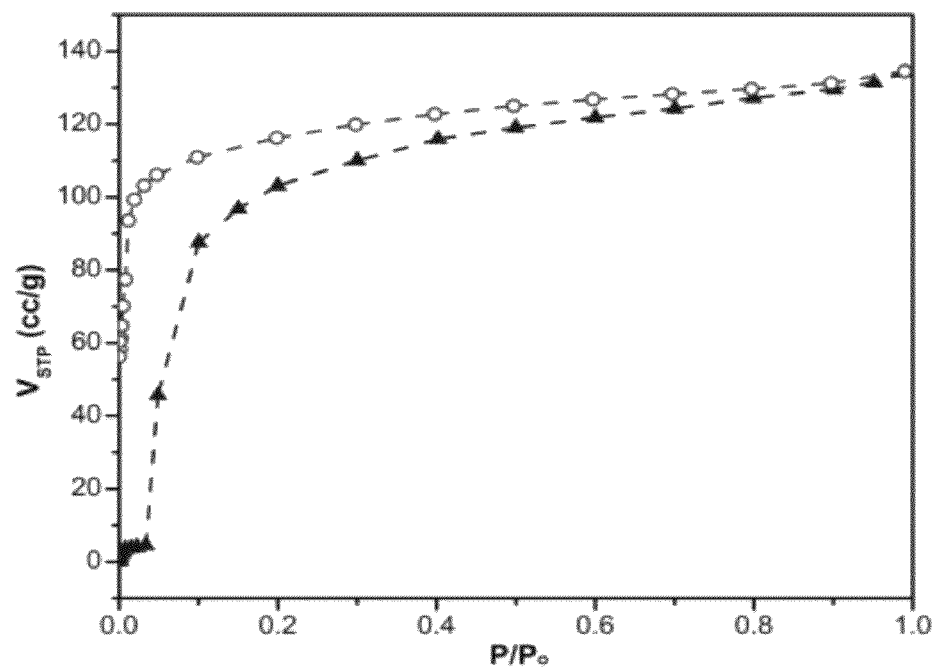
FIG. 8 illustrates argon adsorption (lower curve) and desorption (upper curve) isotherms for a sample of 1' at 87 K.
Figure 9:
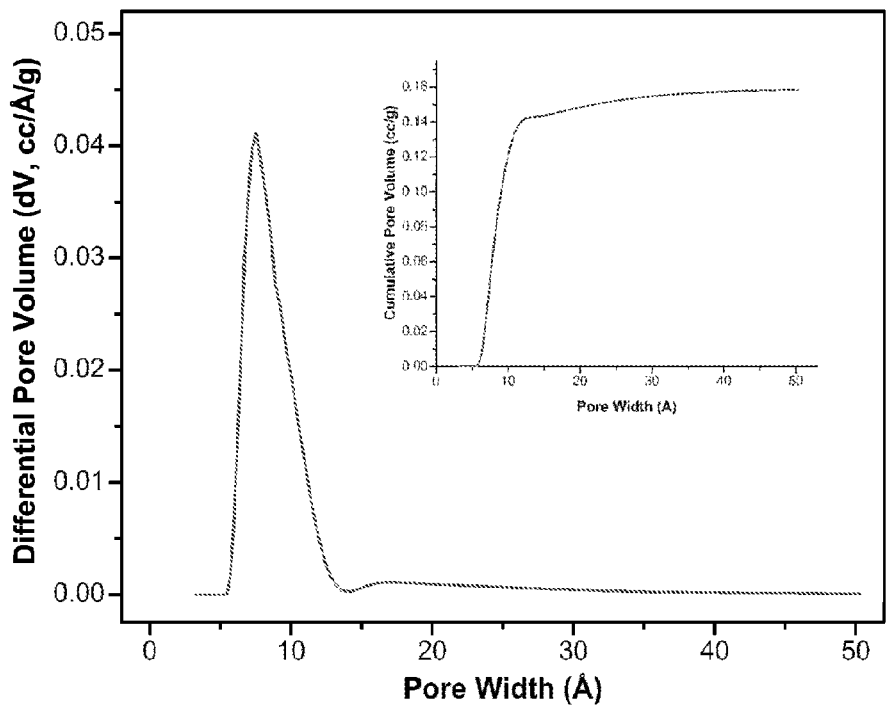
FIG. 9 illustrates the pore size distribution and cumulative (inset) pore volume (cc/g) deduced from the argon sorption results.
Figure 10:
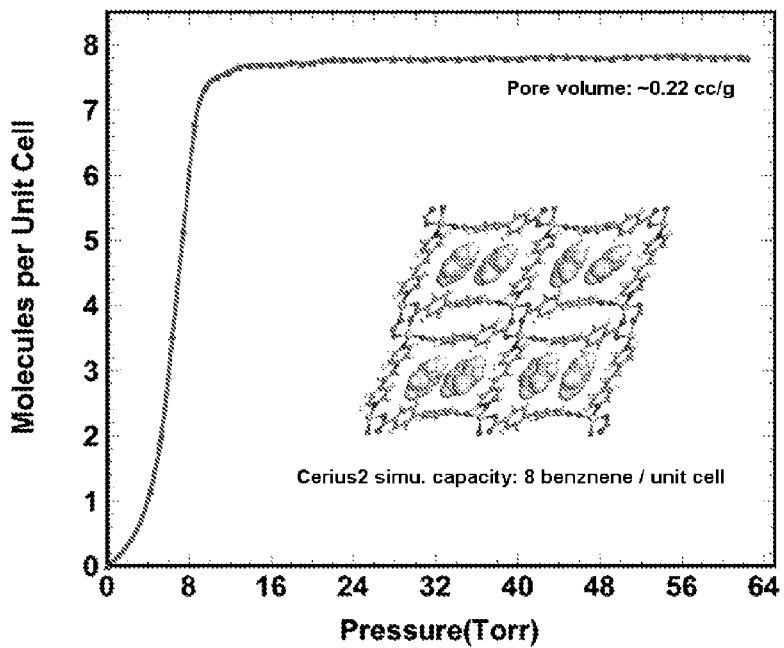
FIG. 10 depicts the benzene adsorption isotherm measured at 50° C. for a sample of 1'. Inset: the simulated uptake of benzene based on the framework structure of 1, showing 8 benzene molecules located in the 4 channel sections within one unit cell.

The gas-sorption measurements were performed on an automated gas adsorption analyzer Autosorb-1 MP (Quantachrome Instruments). The cryogenic temperature (87 K) was obtained using liquid argon as coolant. 97 mg as-made sample of 1 was used for gas sorption studies. The initial activation (outgassing) was performed under high vacuum at 408 K (135° C.) for over-night (about 10~12 hours). The weight loss after activation was 15%, very close to the calculated weight loss of all guest molecules (15.6%). The crystallinity of the activated sample before and after isotherm measurements was double-checked (FIG. 7). Ultra high purity compressed Ar gas (99.995% purity) was used for the experiment. The BET and Langmuir surface areas (328 m$^2$/g and 483 m$^2$/g, respectively) and the total pore volume (0.165 cc/g) were deduced from the argon sorption results (shown in FIG. 8) using the Autosorb v1.55 software. QSDFT pore size distribution was calculated according to the methods described by Ravikovitch and Neimark (*Langmuir*, 2006, 22, 11171-11179).

Example 4

Benzene Adsorption Measurements and Simulations

Adsorption measurements were carried out on a computer controlled thermogravimetric balance consisting of a TA51 electrobalance with associated TA-2000/PC control system, and a series of mass flow controllers and a Eurotherm temperature controller. This flow-through one-atmosphere electrobalance system was controlled by the LabView program through Kinetic Systems Interface. In addition to the experimental adsorption measurements, the Sorption function of the Cerius2 program was used to simulate hydrocarbon vapor-sorption processes.

Both the measured and simulated benzene adsorption capacities correspond to 8 benzene molecules per unit cell. The pore volume estimated from the benzene uptake capacity is about 0.219 cc/g, very close to the 0.222 cc/g calculated by PLATON (A. L. Spek, available via http://www.cryst.chem.uu.nl/platon/platon.). This is considered as another piece of evidence showing the guest-responsive flexibility, in addition to the easy transformation of the structures from that of 1' to 1 described in Example 4.

Figure 11:
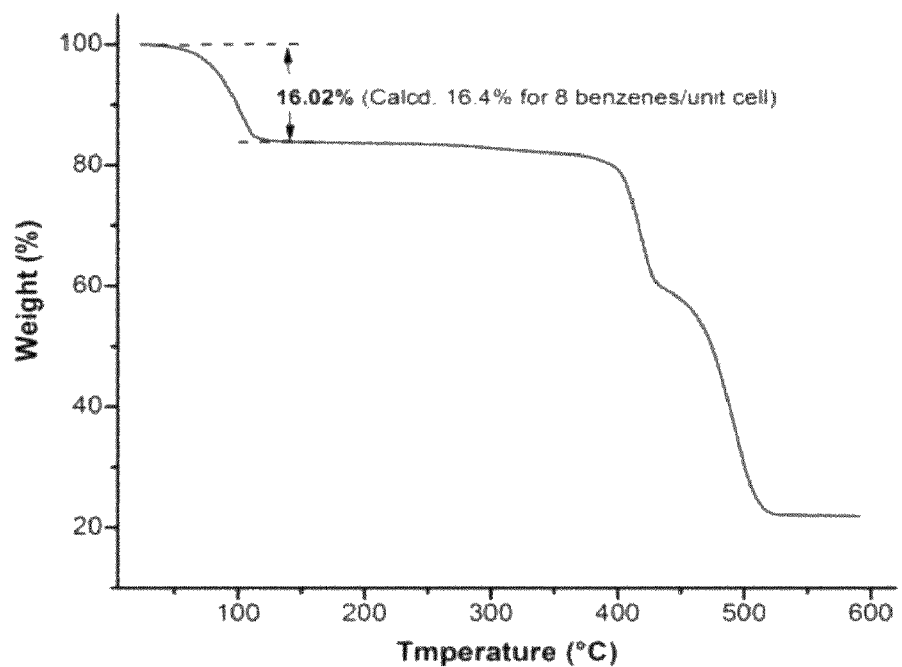
FIG. 11 depicts TGA of a sample of 1' impregnated with benzene.

FIG. 11 shows the TGA of a sample of 1' after being impregnated with benzene (immersed in liquid benzene for 4 days then filtration and drying normally). The observed loss of benzene matches well with the simulated benzene adsorption capacity and the benzene vapor adsorption results.

Example 5

Preparation of Thin Layers

A freshly prepared sample of 1 was immersed in methanol (3 days) and dichloromethane (4 days) before it was filtered and evacuated at room temperature for overnight to afford 1'. The full removal of the guests was confirmed by thermogravimetric analysis. The sample was then carefully ground and kept in a desiccator.

Figure 2:
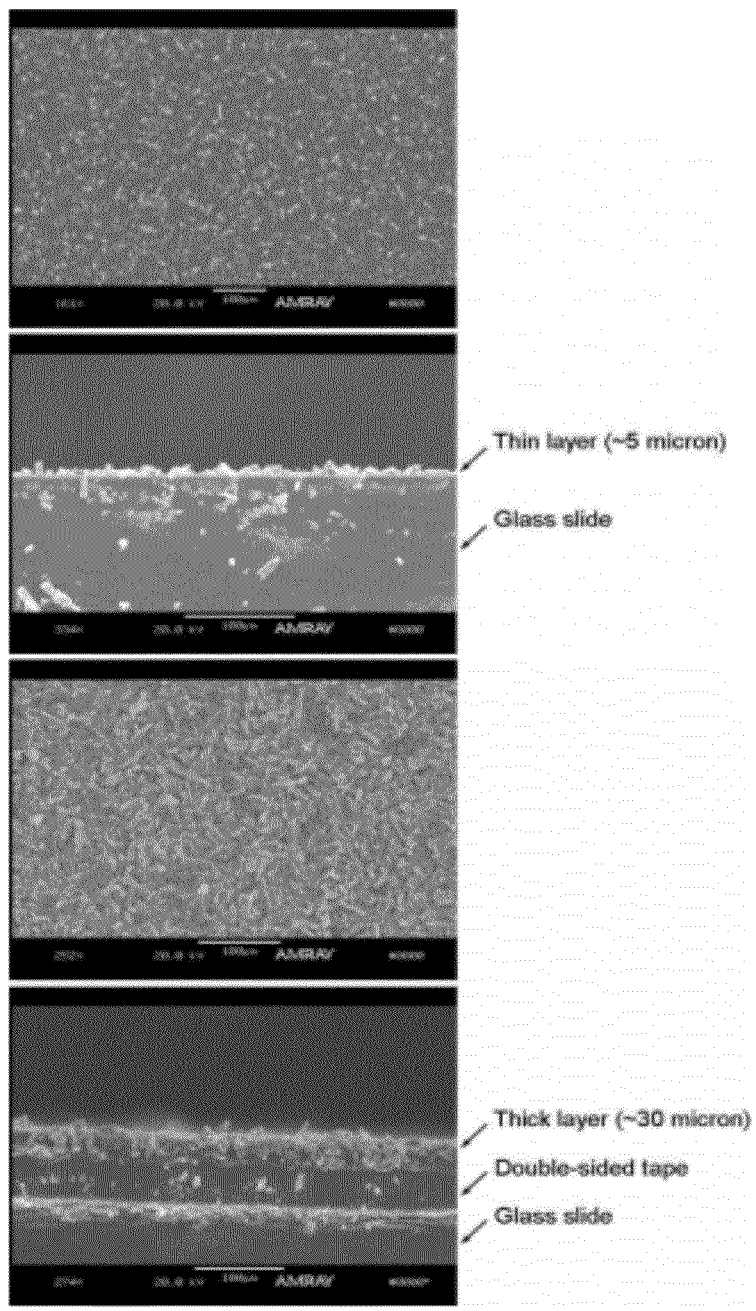
FIG. 2 depicts SEM images of typical thin (top) and thick (bottom) layers of 1' crystals. Scale bars: 100 μm.

Quartz (or glass) slides, 16 mm×60 mm in size, were rinsed by de-ionized water and acetone and dried by nitrogen flow. Double-sided tapes (10 mm×20 mm) were then applied to the lower half of the slides. For making the thin layers of the sample, the tapes were peeled off after a few minutes. The ground powder of 1' was then evenly sprinkled onto the surfaces of the slides. The slides were then turned face-down and gently tapped to remove any powder that was not glued well to the surface of the slides. SEM images (see FIG. 2 in the text) showed that only relatively smaller crystallites were retained in the thin layers (~5-6 µm in thickness) due to the very limited amount of glue left on the slides. While the thin layers are obviously non-continuous, the thick layers (~30 µm in thickness), prepared in a similar fashion as above without peeling off the double-sided tape, are much denser and composed of larger crystallites (the smaller ones are probably buried in between the larger ones and therefore can not be seen clearly in the images).

The fluctuations in the measured maximum intensities are believed to be caused by the non-uniformity and irregular displacement of the thin layers in the sample holder despite effort of minimizing such errors. Such fluctuations, however, do not obscure the trend observed (fluorescence quenching) due to the high sensitivity of 1' to the quenchers.

Example 6

UV-Vis, Excitation and Emission Spectra

Figure 12:
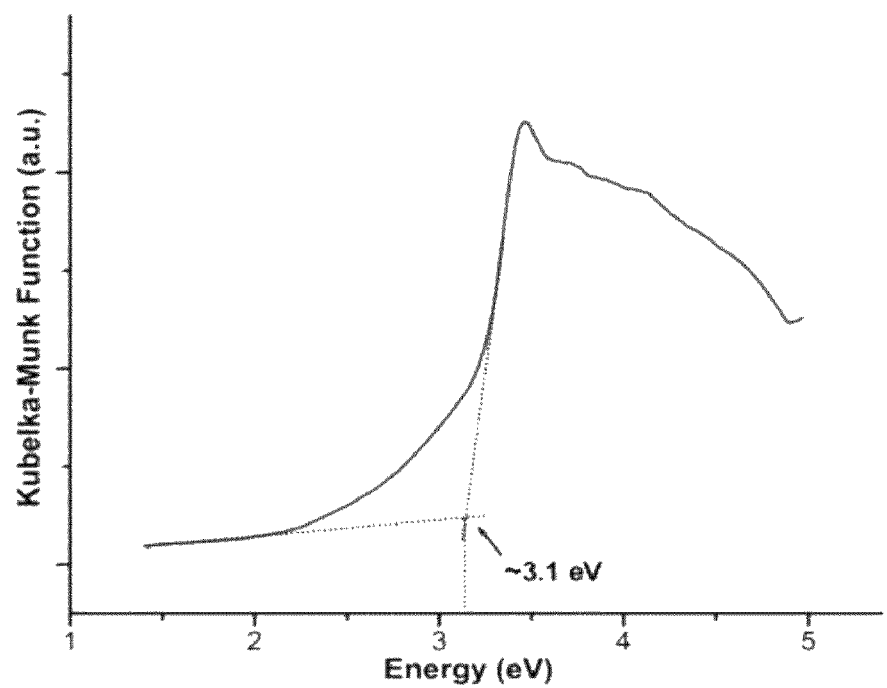
FIG. 12 depicts the band-like diffuse reflectance spectrum of a ground solid sample of 1'. An optical band gap of ~3.1 eV was inferred as indicated.

The UV-Vis absorption spectrum of a ground solid sample of 1' (see Section IV on sample preparation) was collected on a Shimadzu UV-Vis spectrophotometer equipped with an integrating sphere. The diffuse reflectance measured was converted to Kubelka-Munk Function (Z. Tech. Phys., 1931, 12, 593) and the wavelength to eV. The optical band gap was estimated, as indicated in FIG. 12, to be ~3.1 eV.

Figure 13:
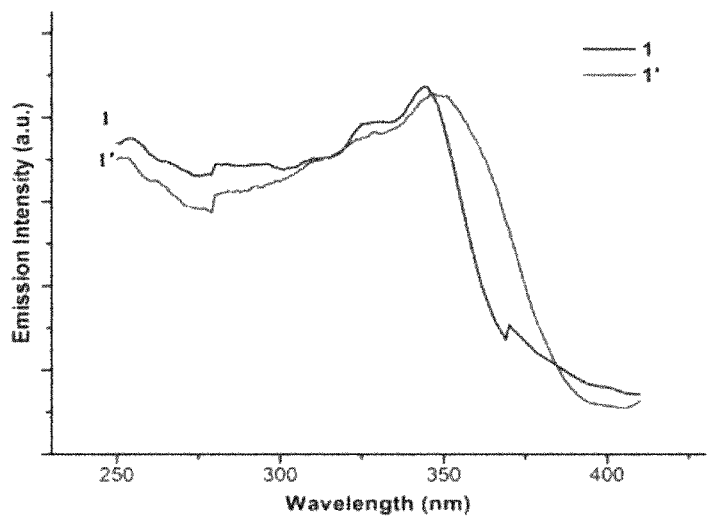
FIG. 13 depicts excitation spectra of ground samples of 1 and 1', at the emission maxima of 454 nm and 420 nm, respectively.

The excitation and emission spectra of thin layers of 1 and 1' were measured on a Varian Cary Eclipse fluorescence spectrophotometer. The excitation spectra were obtained by varying excitation energy while fixing the emission wavelengths at 454 nm and 420 nm, the emission maxima of 1 and 1' respectively (FIG. 13). The broad and flat band-like spectra for both indicate minimal dependence of the emission intensity on the excitation wavelength, which was confirmed by the emission spectra taken.

Figure 14:
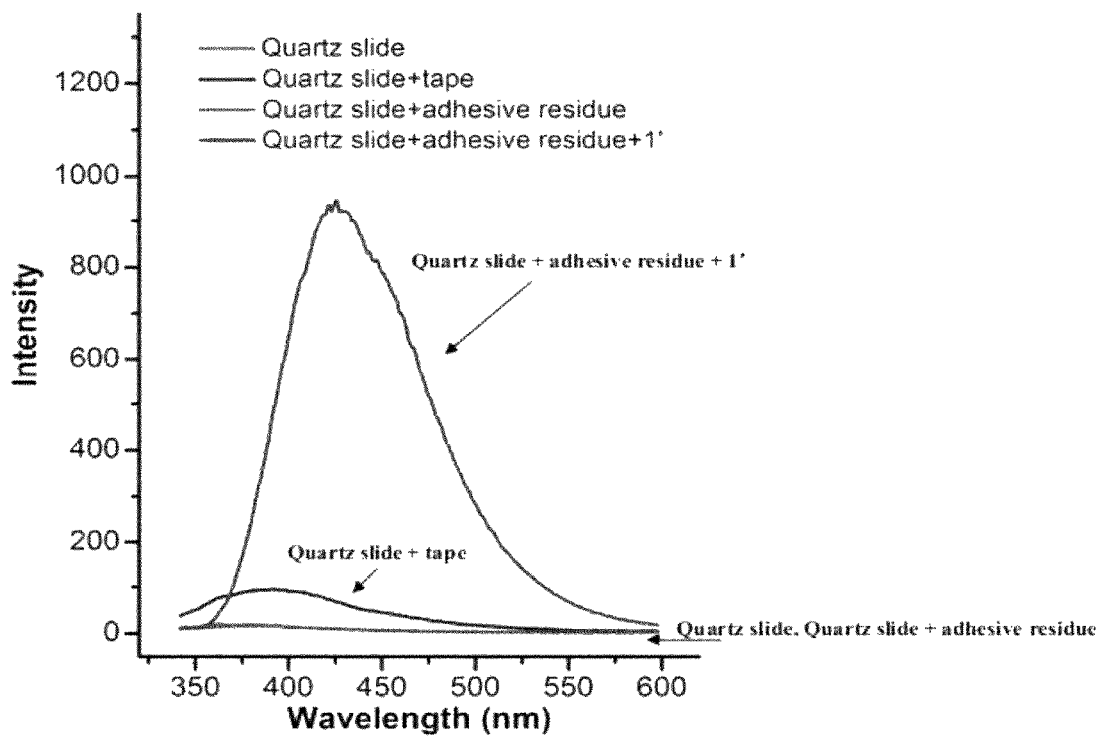
FIG. 14 illustrates a comparison of the photoluminescence from the slide, the tape and the adhesive residue, as well as 1'.
Figure 15:
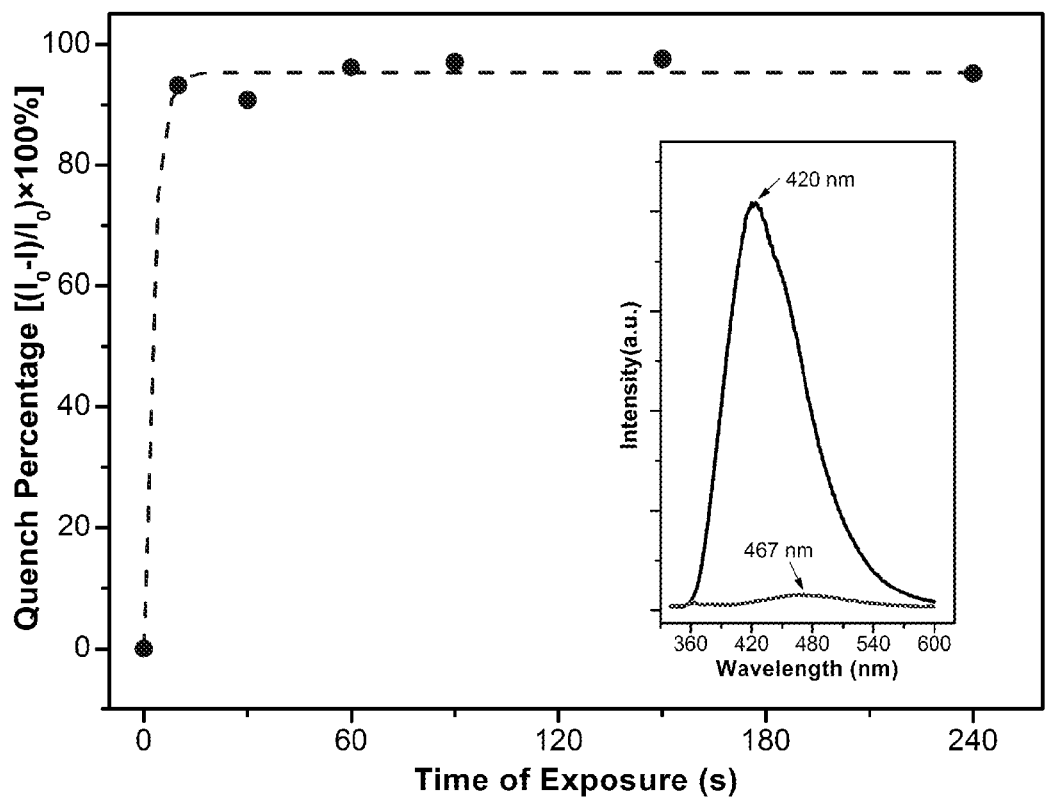
FIG. 15 illustrates fluorescence quenching profile for BQ.
Figure 16:
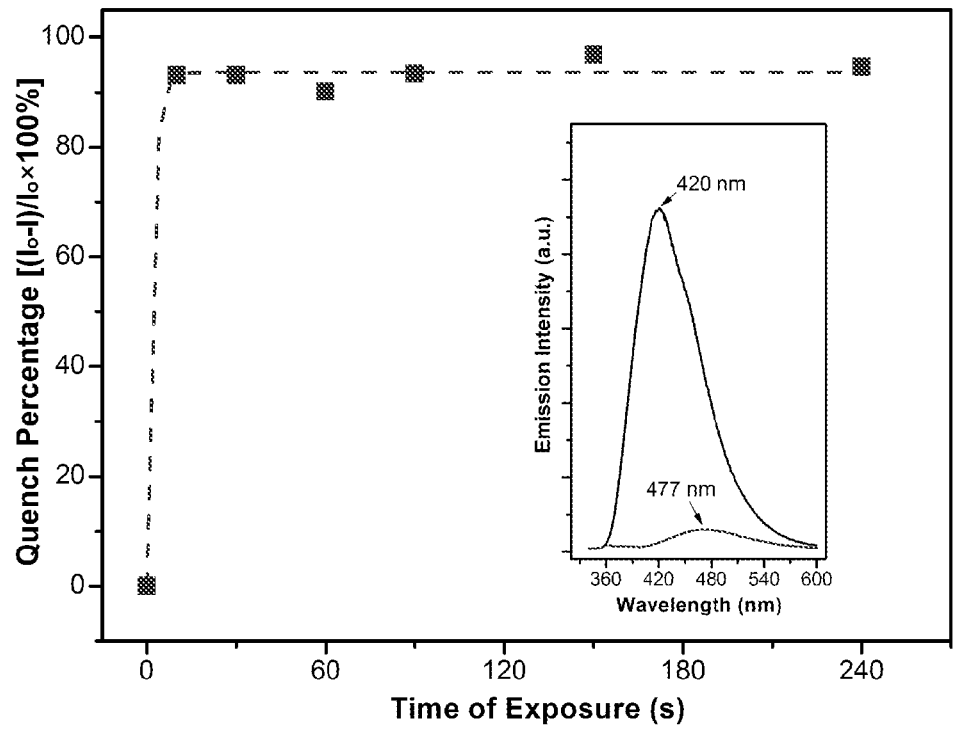
FIG. 16 illustrates fluorescence quenching profile for NB.
Figure 17:
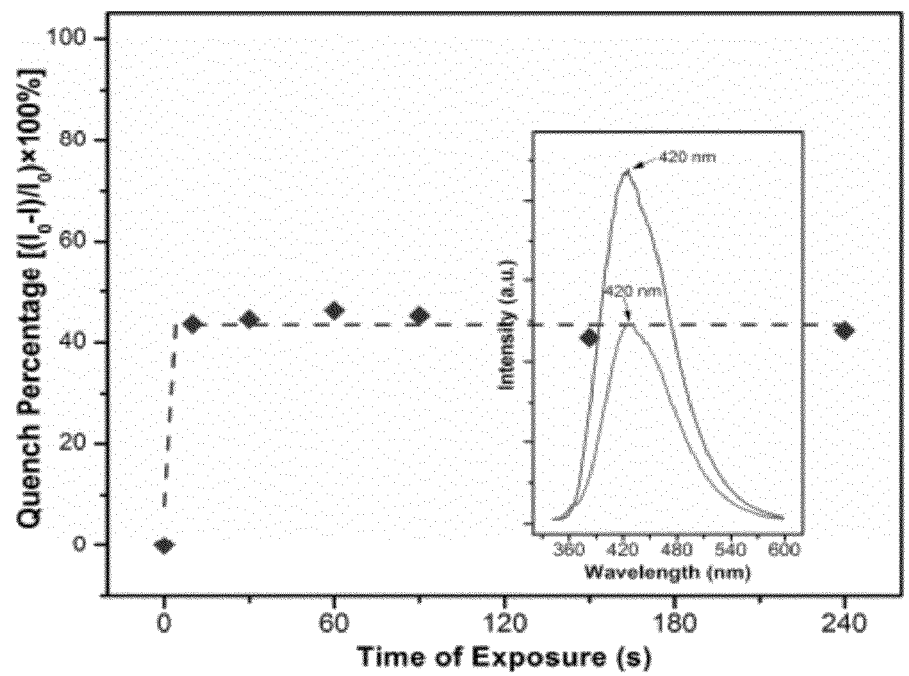
FIG. 17 illustrates fluorescence quenching profile for benzene.
Figure 18:
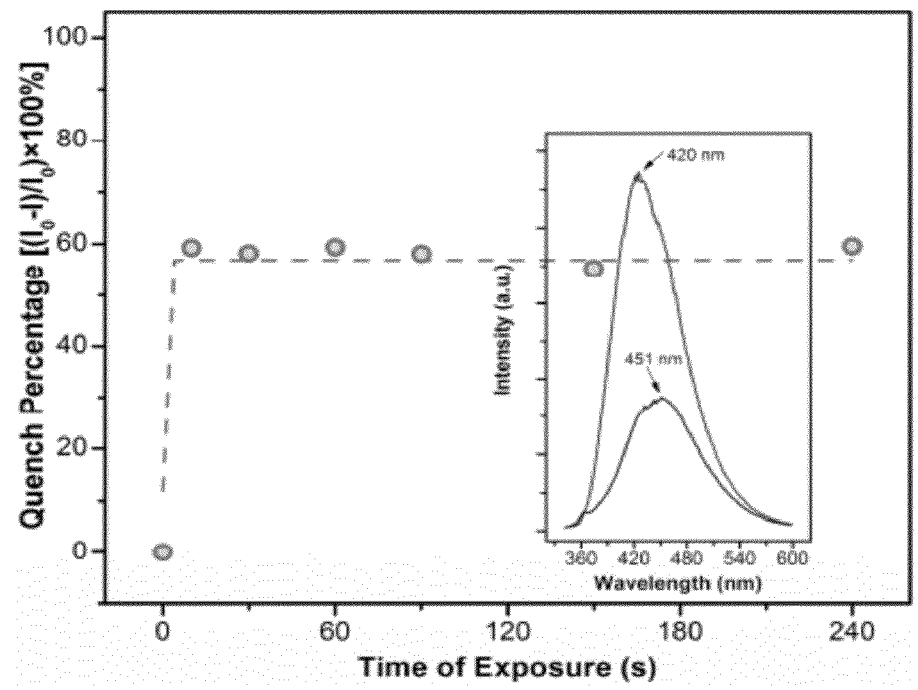
FIG. 18 illustrates fluorescence quenching profile for DMF.

In order to investigate if the double-sided tape or the adhesive residue (after peeling off the tape) would affect the photoluminescence of 1'. Their photoluminescence spectra were also measure and compared with that of 1' in FIG. 14.

FIGS. 15-18 show the fluorescence quench profiles by vapors of nitrobenzene (NB), benzoquinone (BQ), benzene (B), and N,N-dimethylformamide (DMF). Coincidentally, BQ and NB show almost identical and the highest fluorescence quench (~94%). Redshift of the fluorescence wavelengths to ~467 nm to ~477 nm are also observed, respectively for BQ and NB. Note that DMF also quenches the fluorescence of 1' (~58%) with a redshift of the emission maxima to ~451 nm. Benzene quenches the least of the fluorescence of 1' (~45%) and no obvious shift of the emission maxima is observed.

Figure 19:
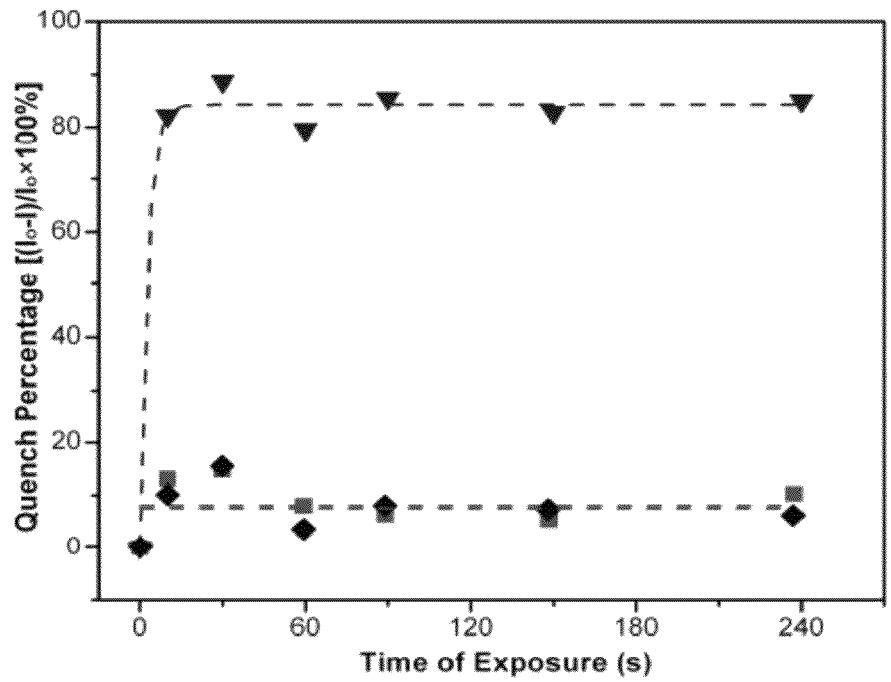
FIG. 19 illustrates DMNB quench of the fluorescence of thin layers of 1' (triangle), 1 (diamond) and benzene-impregnated 1' (square).

Thin layers were also prepared from 1 (with DMF) and benzene-impregnated 1' and their fluorescence quenching by DMNB were measured. The results are shown in FIG. 19. While 1' shows significant quenching (~84%), 1 and benzene-impregnated 1' show similarly low quench (<10%). Because the internal surfaces of these samples have been occupied by benzene or DMF, the observed quench can be attributed to the DMNB adsorbed to the external surfaces of the crystals. Although benzene and DMF inside the pores also quench the fluorescence of 1', the similar behavior of these two samples to DMNB, when compared to that of 1', may be considered as indirect evidence indicating that pore confinement effect enhances the quenching effect.

Figure 20:
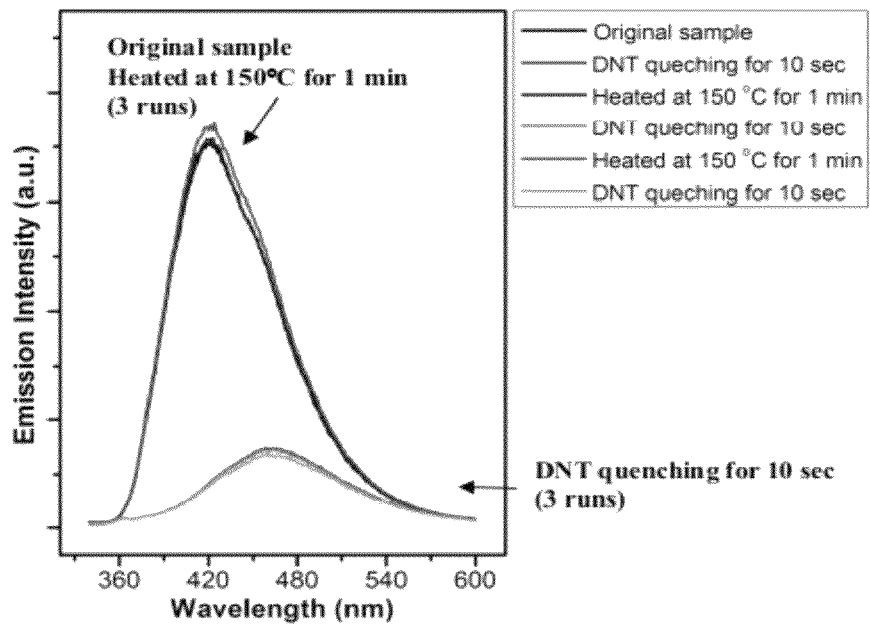
FIG. 20 depicts emission spectra of a thin layer of 1' in three consecutive quenching (by DNT vapor)/regeneration (150° C. for 1 min) cycles.
Figure 21:
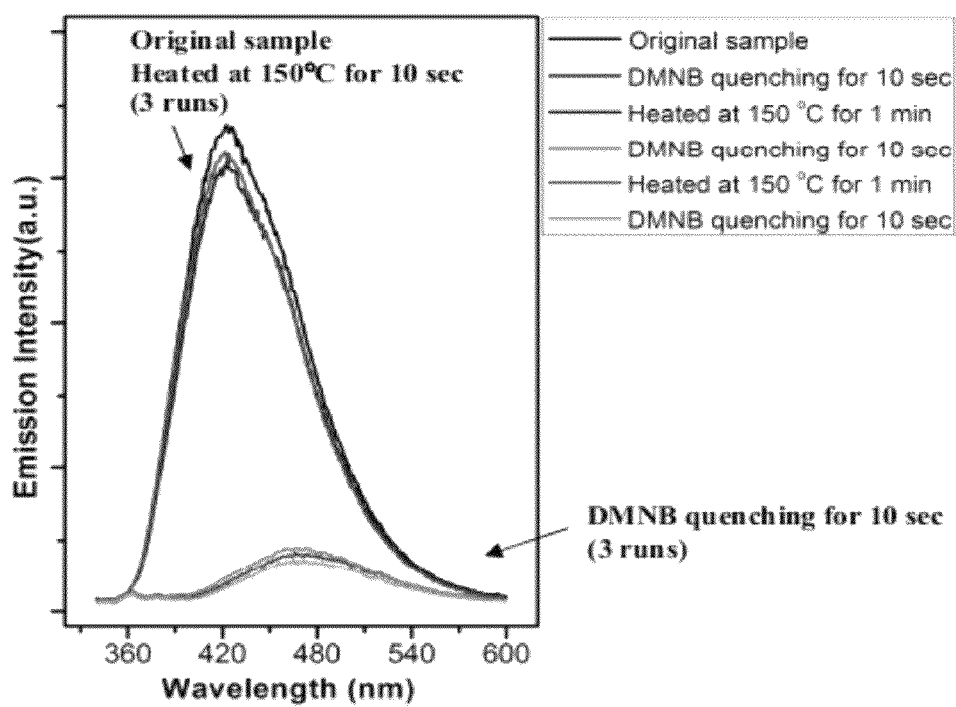
FIG. 21 depicts emission spectra of a thin layer of 1' in three consecutive quenching (by DMNB vapor)/regeneration (150° C. for 1 min) cycles.

FIGS. 20 and 21 depict the fluorescence response of the pristine and regenerated layers towards vapors of DNT and DMNB. The results show that 1' can be used as a fully reversible optical sensor for detection of explosive vapors.

The recyclability of the samples was examined by re-heating them for a period of time and then re-test them under otherwise identical conditions to those in the initial run. The results for three runs are plotted in FIGS. 20 and 21. Data demonstrates that the process is highly reproducible, and the material can be re-used for detecting explosive compounds, for example, DNT and DMNB, after brief heating.

The structure of 1 contains 1D roughly rectangular-shaped channels where DMF solvent molecules are encapsulated, which can be removed either by heating under vacuum for an extended period of time or by pumping at room temperature following solvent exchange with methanol and dichloromethane. Both treatments resulted in the same crystalline guest-free material. Guest-free 1 (referred as 1' hereafter) was confirmed by argon adsorption measurements to have a pore volume of 0.17 $cm^3 g^{-1}$, a narrow QSDFT (P. I. Ravikovitch and A. V. Neimark, *Langmuir* 2006, 22, 11171) pore size distribution around 7.5 Å and a Langmuir surface area of 483 $m^2 g^{-1}$ (Example 3). Distortion of the unit cell, as indicated by the shifts of the PXRD peaks, was observed accompanying removal of DMF. The distorted structure of 1' can be reversed to the original structure by reintroducing DMF under mild conditions (Example 2). The fact that the measured amount of benzene adsorbed by a sample of 1' matches well with the simulated benzene uptake (based on the framework structure of 1), both corresponding to ca. 8 benzene molecules per unit cell, also suggests the easy transition between the two structures (Example 4). This type of guest-responsive changes in MMOF structures has been well documented and considered as a beneficial feature for advanced applications. (C. A. Bauer, et al., *J. Am. Chem. Soc.* 2007, 129, 7136; T. K. Maji, et al., *Nat. Mater.* 2007, 6, 142; D. Tanaka, et al., *Angew. Chem. Int. Ed.* 2008, 47, 3914; N. Yanai, et al., *J. Am. Chem. Soc.* 2007, 129, 3496; T. K. Maji and S. Kitagawa, *Pure Appl. Chem.* 2007, 79, 2155).

1' is highly luminescent in solid-state at room temperature. $H_2$ bpdc and bpee were chosen to build luminescent MMOFs targeted for sensing applications because their highly conjugated π-systems could act as both the sources of the luminescence and the chemical recognition elements (binding sites). As expected, 1' appears very bright to the eye when illuminated by a UV lamp (at 254, 304 and 350 nm). It was confirmed that the emission peak wavelengths and intensities are independent of the excitation wavelength between 260 nm and 340 nm, which can be explained by the broad and flat absorption bands and excitation spectra that cover the same region (Example 6). In order to demonstrate the capability of 1' for explosives detection, the fluorescence spectra of thin layers (ca. 5 μm, FIG. 2, top) of 1' were monitored, before and after exposing them to the equilibrated vapors of DNT (ca. 0.18 ppm at 25° C.) and DMNB (ca. 2.7 ppm at 25° C.) for varied periods of time (10 s, 30 s, 60 s, 90 s, 150 s and 240 s, see Example 5 for the preparation of the layers).

Figure 3:
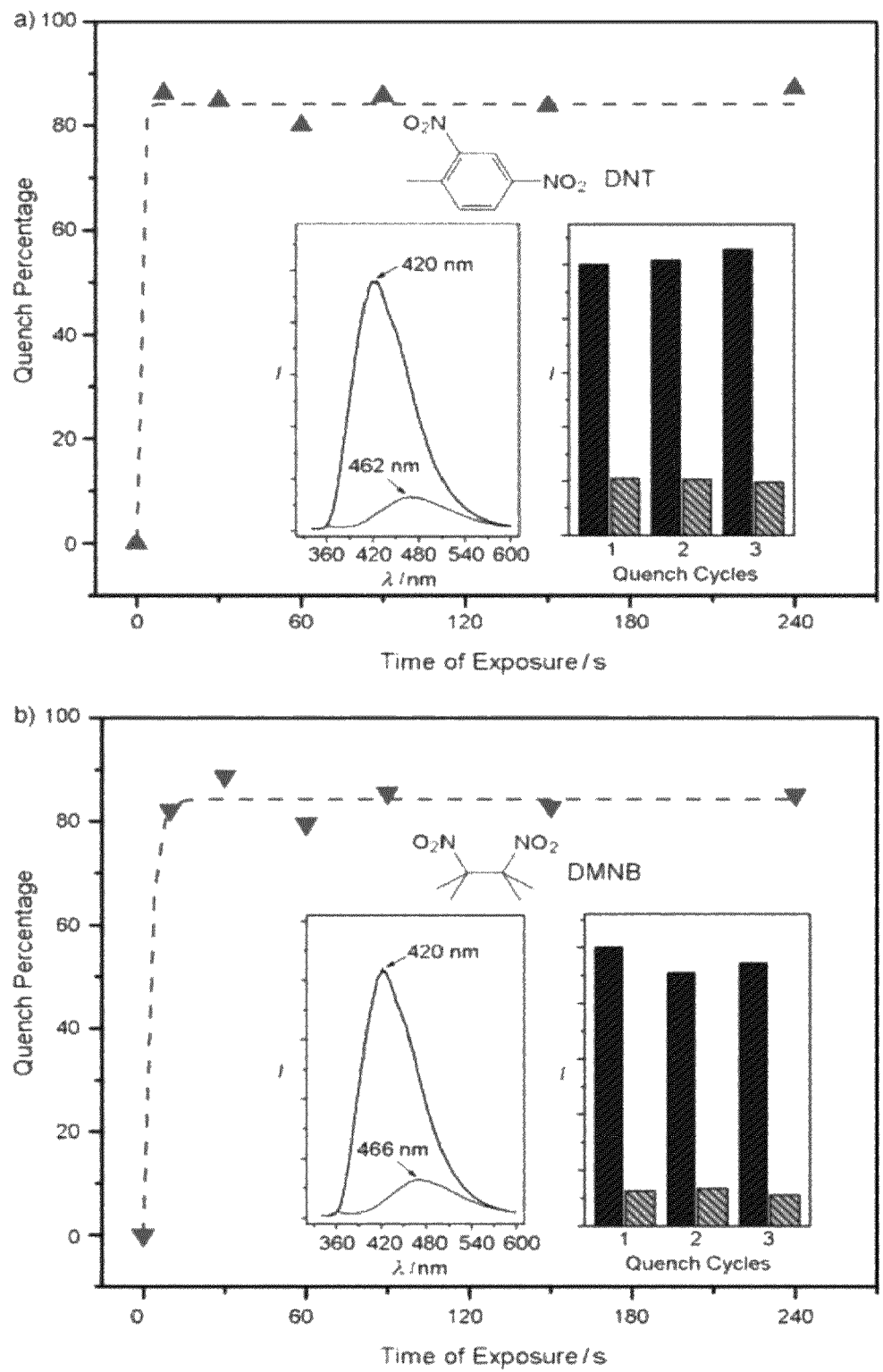
FIG. 3 illustrates time-dependent fluorescence quenching by 2,4-dinitrotoluene (DNT) and 2,3-dimethyl-2,3-dinitrobutane (DMNB) (Ex.: 320 nm). Insets: the corresponding fluorescence spectra before and after exposure to the analyte vapors for 10 s (left) and three continuous quench/regeneration cycles (right).

As shown in FIG. 3, 1' showed almost identically rapid and evident responses to both of the chemicals tested. Within 10 seconds, the fluorescence quench percentages (defined as $(I_o-I)/I_o \times 100\%$, $I_o$: original peak maximum intensity, I: maximum intensity after exposure) reached almost the maxima for both DNT and DMNB (ca. 85% and 84%, respectively). No further quenching was observed with extended exposure. While this degree of sensitivity to DNT vapor is comparable to that of the best performing conjugated polymer (CP) thin films, 1' appears to respond to the quenchers more quickly and it also outperforms in its unprecedentedly high sensitivity towards DMNB in vapor phase. (S. W. Thomas, et al., *Chem. Rev.* 2007, 107, 1339; S. Y. Tao, et al., *J. Mater. Chem.* 2006, 16, 4521). There are only two other materials reported so far to be able to detect DMNB vapors, exhibiting ~40% (90 nm thick film, 10 s exposure; ~73% quench at 2 min in sealed cuvette) (T. Naddo, et al., *Sensors and Actuators, B: Chemical* 2008, 134, 287) and ~20% quench (film thickness unknown, 20 s exposure) (S. W. Thomas, et al., *Chem. Commun.* 2005, 4572), respectively. In addition, detections of both DNT and DMNB with 1' are fully reversible. After quenching, the photoluminescence of 1' can be recovered by simply heating the layer at 150° C. for about 1 minute (FIG. 3 and Example 6). There are obvious redshifts of the fluorescence peaks upon exposure to DNT and DMNB (FIG. 3). Such a peak shifting is also observed with other analytes (see Example 6), indicative of guest-dependent interactions between the MOF host framework and the analytes.

Figure 4:
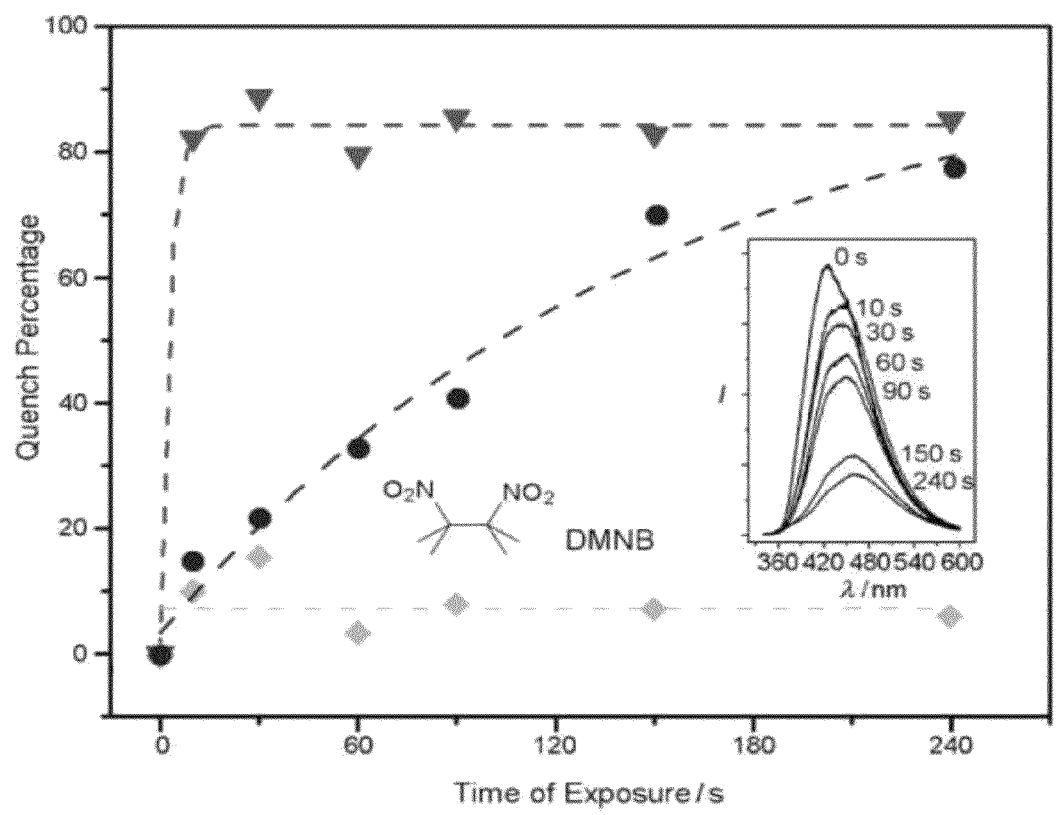
FIG. 4 illustrates a comparison of the time-dependent fluorescence quenching by DMNB for thin layers (triangles, grey), thick and dense layers (circles, dark grey) of 1', and thin layers of 1 (diamonds, light grey). Insert: the fluorescence spectra for a thick layer of 1' at the specified exposure time.

The outstanding sensing capability of 1' may be attributed to its infinite 3D framework structure and the inherent microporosity. It has been shown in the studies of conjugated polymer thin films and other sensing materials that higher dimensionality enhances sensitivity because the excitons can be quenched by greater numbers of analyte binding sites through delocalization over the conjugated polymer backbone ("molecular wire" effect), via interchain energy migration in the solid state (films or aggregates), or through highly organized molecular stacking structure. (S. W. Thomas, et al., *Chem. Rev.* 2007, 107, 1339; T. Naddo, et al., *Sensors and Actuators, B: Chemical* 2008, 134, 287). Analogously, the extended three-dimensional network structure of 1' containing ordered π moieties may also facilitate the migration of the excitons through similar mechanisms. The large optical band gap (ca. 3.1 eV) indicates that the framework in the excited state is highly reductive, providing adequate driving force for the electron transfer to the DNT and DMNB quenchers. (S. W. Thomas, et al., *Chem. Commun.* 2005, 4572; T. Naddo, et al., *Sensors and Actuators, B: Chemical* 2008, 134, 287). The effect of the microporosity in 1' is two fold. Porous structure has been proven to be a favorable feature for the fast detection of explosive vapors by the AFP (Amplifying Fluorescent Polymer) films (S. W. Thomas, et al., *Chem. Rev.* 2007, 107, 1339), metalloporphyrin-doped mesostructured silca films (S. Y. Tao, et al., *J. Mater. Chem.* 2006, 16, 4521), and fluorescent nanofibril films. (T. Naddo, et al., *J. Am. Chem. Soc.* 2007, 129, 6978; T. Naddo, et al., *Sensors and Actuators, B: Chemical* 2008, 134, 287). The readily accessible micropores in 1' and the fully exposed internal surface of a high Langmuir surface area of 483 $m^2$ $g^{-1}$ provide facile diffusion routes and binding sites for the vapors, accounting for the very quick responses (ca. 10 s). Another evidence showing the importance of the microporosity is that thin layers of 1 (with pores occupied by DMF solvent molecules) showed dramatically lower responses to DMNB vapor (ca. 8%). In this case, the quench occurs only at the external surfaces of the MOF, since the pores are already filled by DMF (FIG. 4).

As expected, thicker (and much denser) layers (ca. 30 μm, FIG. 2) of 1' showed slower fluorescence quenching responses due to restricted diffusion. Similar dependence on film thickness was also observed in the CP films. However, it should be noted that the quench percentages observed for the thicker (and denser) layers, given enough exposure time, approach the same level for the thin layers. This behavior is in contrast to the CP films, for which the quench efficiency normally plummets with increasing film thickness. (T. Naddo, et al., *Sensors and Actuators, B: Chemical* 2008, 134, 287). This also suggests that further reducing the size of the crystals of 1' and the thickness of the layers should result in even faster responses but probably not higher sensitivity.

The excellent fluorescence quenching response to DMNB can be further attributed to the pore confinement of the analyte inside the molecular-sized cavities of 1' which facilitates stronger interactions between the DMNB and the host framework. This is reflected by the relatively small difference in the quench percentages for nitrobenzene (NB) which exhibits only ~10% higher sensitivity (94% quench at 10 s) compared to DMNB (Example 6), despite drastic differences in their vapor pressures (ca. 300 ppm for NB vs 2.7 ppm for DMNB at 25° C.) and reduction potentials (−1.15 V for NB vs −1.7 V for DMNB), in addition to the flat structure of NB that favors strong π-π interaction with the framework. (J.-S. Yang and T. M. Swager, *J. Am. Chem. Soc.* 1998, 120, 11864; J.-S. Yang and T. M. Swager, *J. Am. Chem. Soc.* 1998, 120, 5321). This effect may also account for the almost identical responses of 1' to DNT and DMNB although DNT has a more favorable reduction potential (−1.0 V vs SCE) and π-type interactions. (J.-S. Yang and T. M. Swager, *J. Am. Chem. Soc.* 1998, 120, 11864; J.-S. Yang and T. M. Swager, *J. Am. Chem. Soc.* 1998, 120, 5321). A comparison of quench response of 1' with benzene (~45%, $1.3 \times 10^5$ ppm at 25° C.) and DMF (~58%, $1 \times 10^4$ ppm at 25° C.) vapors indeed suggests a degree of its selectivity towards different analyte species. Similar to the CPs, 1' exhibits stronger responses to the more electron-deficient compounds (e.g., NB, DNT and DMNB).

In summary, a highly luminescent MMOF, [$Zn_2(bpdc)_2(bpee)$], was designed and successfully synthesized. It is the first microporous crystalline metal-organic material demonstrated to be able to detect trace explosives in vapor phase, probably through a redox quenching mechanism similar to that in the conjugated polymer systems. Very fast responses and high sensitivity towards representative nitroaromatic explosive, DNT, and plastic explosive taggant, DMNB, were observed. The 84% fluorescence quench efficiency by DMNB after merely 10 second exposure is unprecedented. Furthermore, such detections were also proven to be reversible. These remarkable preliminary results point to a new and important application of microporous metal organic framework materials.

One of ordinary skill in the art guided by this disclosure can develop a series of luminescent MMOFs (with different framework structures, band gaps, pore size/shape/nature, and etc.) that will have different responses towards the same analyte. By combining these MMOFs into a sensor array, fingerprint like response pattern to each analyte is attainable. (M. E. Germai and, M. J. Knapp, *J. Am. Chem. Soc.* 2008, 130, 5422; K. J. Albert, et al., *Chem. Rev.* 2000, 100, 2595). Considering the vast versatility of this type of materials, highly sensitive and selective sensors or sensor arrays based on luminescent MMOFs can be prepared.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

What is claimed is:

1. A polymeric coordination compound capable of forming a microporous metal organic framework (MMOF), characterized by a plurality of layers comprising two-dimensional arrays of repeating structural units, each repeating structural unit comprising at least one transition metal atom or cation (M) coordinated to:

at least one binding member of a bisphenyl-dicarboxylate (bpd) bidentate binding site on each of two polyfunctional ligands of formula (I):

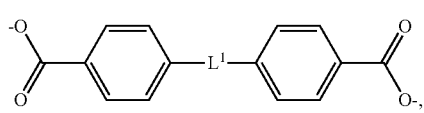

wherein $L^1$ is a bond, —$CH_2$—, —$CHR^1$—$CHR^2$—, or —$CR^1$=$CR^2$—, wherein $R^1$ and $R^2$ are each independently hydrogen (H), methyl, or ethyl group;

one binding site of a bis-pyridine (bp) exodentate bridging ligand of formula (II):

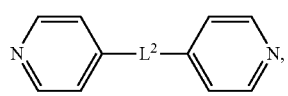

wherein $L^2$ is a —$CH_2$—, —$CHR^1$—$CHR^2$—, or —$CR^1$=$CR^2$—, wherein $R^1$ and $R^2$ are each independently hydrogen (H), methyl, or ethyl group; and said microporous framework has the stoichiometric formula [$M_2(bpd)_2(bp)$], optionally comprising one or more solvent molecules;

wherein:

(i) at least one binding member of a second bidentate binding site on each polyfunctional ligand is further coordinated to at least one transition metal atom in a different repeating structural unit within the same layer containing a two-dimensional array of repeating structural units;

(ii) the bis-pyridine exodentate bridging ligand extends essentially perpendicularly from a plane defined by said layer containing a two-dimensional array of repeating structural units to further coordinate with a transition metal atom in a repeating structural unit in an adjacent layer; and (iii) the ligands of the three-dimensional MMOF define channels and pores of molecular size throughout the structure of the compound.

2. The polymeric coordination compound of claim 1, wherein $L^1$ is a bond.

3. The polymeric coordination compound of claim 1, wherein $L^2$ is —$CR^1$=$CR^2$—, wherein $R^1$ and $R^2$ are each independently H, methyl, or ethyl group.

4. The polymeric coordination compound of claim 1, wherein the transition metal M is $Zn^{2+}$ or $Cd^{2+}$.

5. The polymeric coordination compound of claim 1, wherein:

(a) the ligand of formula (I) is 4,4'-biphenyldicarboxylate (bpdc);
(b) the ligand of formula (II) is 1,2-bipyridylethene (bpee) or 1,2-bipyridylethane (bpe);
(c) the transition metal (M) is $Zn^{2+}$ or $Cd^{2+}$; and
(d) said polymeric coordination compound is luminescent and capable of changing luminescence when in contact with vapors of an explosive compound.

6. The polymeric coordination compound of claim 5, characterized by formula [$M_2(bpdc)_2(bpee)$].

7. The polymeric coordination compound of claim 6, wherein M is $Zn^{2+}$ or $Cd^{2+}$.

8. The polymeric coordination compound of claim 1, wherein said MMOF is luminescent and capable of detecting an explosive compound comprising one or more nitro (—$NO_2$) groups.

9. The polymeric coordination compound of claim 8, wherein said explosive compound is selected from 2,4-dinitrotoluene (DNT), 2,4,6-trinitrotoluene (TNT), 2,3-dimethyl-2,3-dinitrobutane (DMNB), and cyclotrimethylenetrinitramine (RDX).

10. A method of preparing a polymeric coordination compound of claim 1, comprising heating a mixture comprising a transition metal salt (M), a ligand of formula (I), and a ligand of formula (II) in a solvent for a period time until a block-like crystal is formed.

11. The method of claim 10, wherein said polymeric coordination compound comprises a structure of formula [M$_2$(bpdc)$_2$(bpee)], which optionally comprises one or more solvent molecules, wherein bpdc is 1,4-biphenyldicarboxylic acid, and bpee is 1,2-bipyridylethene.

12. The method of claim 10, wherein said transition metal salt is zinc nitrate (Zn(NO$_3$)$_2$) or a solvate thereof.

13. The method of claim 10, wherein said block-like crystal comprises a three-dimensional (3-D) framework structure in monoclinic space group C2/c.

14. The method of claim 10, wherein said block-like crystal comprises a structure of formule [Zn$_2$ (bpdc)$_2$ (bpee)] having a 3-D structure in monoclinic space group C2/c.

15. A method of detecting an explosive compound in a subject, the method comprising:
(a) exposing the subject to a polymeric coordination compound capable of forming a microporous metal organic framework (MMOF) characterized by a plurality of layers comprising two-dimensional arrays of repeating structural units, each repeating structural unit comprising at least one transition metal atom or cation (M) coordinated to:
at least one binding member of a bisphenyl-dicarboxylate (bpd) bidentate binding site on each of two polyfunctional ligands of formula (I):

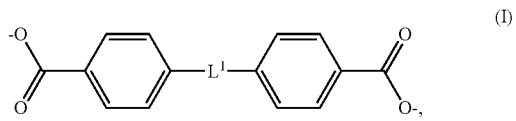

(I)

wherein L$^1$ is a bond, —CH$_2$—, —CHR$^1$—CHR$^2$—, or —CR$^1$═CR$^2$—, wherein R$^1$ and R$^2$ are each independently hydrogen (H), methyl, or ethyl group; and
one binding site of a bis-pyridine (bp) exodentate bridging ligand of formula (II):

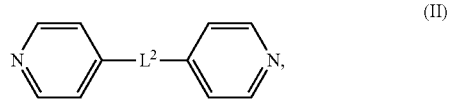

(II)

wherein L$^2$ is a —CH$_2$—, —CHR$^1$—CHR$^2$—, or —CR$^1$═CR$^2$—, wherein R$^1$ and R$^2$ are each independently hydrogen (H), methyl, or ethyl group;
wherein:
(i) at least one binding member of a second bidentate binding site on each polyfunctional ligand is further coordinated to at least one transition metal atom in a different repeating structural unit within the same layer containing a two-dimensional array of repeating structural units;
(ii) the bis-pyridine exodentate bridging ligand extends essentially perpendicularly from a plane defined by said layer containing a two-dimensional array of repeating structural units to further coordinate with a transition metal atom in a repeating structural unit in an adjacent layer; and
(iii) the ligands of the three-dimensional MMOF define channels and pores of molecular size throughout the structure of the compound; and
(b) observing and/or measuring the change of the luminescence of the polymeric coordination compound,
wherein said polymeric coordination compound is luminescent and capable of changing luminescence when in contact with vapors of an explosive compound, and wherein a decreased intensity of the luminescence of the polymeric coordination compound indicates that the subject potentially contains an explosive compound.

16. The method of claim 15, wherein:
L$^1$ is a bond, —CH$_2$—, —CH═CH— or —CH$_2$CH$_2$—; and
L$^2$ is —CR$^1$═CR$^2$—, wherein R$^1$ and R$^2$ are each independently hydrogen (H), methyl, or ethyl group.

17. The method of claim 15, wherein said MMOF comprises a repeating unit comprising a structure of formula [M$_2$(bpdc)$_2$(bpee)] (bpdc=4,4'-biphenyldicarboxylate; bpee=1,2-bipyridylethene), optionally comprising one or more solvent molecules, wherein M is a transition metal cation.

18. The method of claim 15, wherein M is Zn$^{2+}$ or Cd$^{2+}$.

19. The method of claim 15, wherein M is Zn$^{2+}$, and wherein said MMOF comprises a three-dimensional structure in monoclinic space group C2/c.

20. The method of claim 15, wherein said explosive compound comprises one or more nitro (—NO$_2$) groups.

21. The method of claim 15, wherein said explosive compound is selected from the group consisting of 2,4-dinitrotoluene (DNT), 2,4,6-trinitrotoluene (TNT), 2,3-dimethyl-2,3-dinitrobutane (DMNB), and cyclotrimethylenetrinitramine (RDX).

22. A sensor or sensor array for detection of explosive compounds comprising a polymeric coordination compound of claim 1.

23. The sensor or sensor array of claim 22, wherein said polymeric coordination compound comprises a repeating unit characterized by formula [M$_2$(bpdc)$_2$(bpee)] (bpdc=4,4'-biphenyldicarboxylate; bpee=1,2-bipyridylethene), wherein M is a transition metal cation, and wherein said polymeric coordination compound is luminescent and capable of changing luminescence when in contact with vapors of an explosive compound.

24. The sensor or sensor array of claim 22, wherein the transition metal is Zn$^{2+}$ or Cd$^{2+}$.

25. The sensor or sensor array of claim 22, wherein M is Zn$^{2+}$ and said polymeric coordination compound comprises a three-dimensional structure in monoclinic space group C2/c.

* * * * *